(12) United States Patent
Hochwalt

(10) Patent No.: US 11,896,731 B2
(45) Date of Patent: Feb. 13, 2024

(54) METHODS OF DISARMING VIRUSES USING REACTIVE GAS

(71) Applicant: NanoGuard Technologies, LLC, St. Louis, MO (US)

(72) Inventor: Mark A. Hochwalt, Chesterfield, MO (US)

(73) Assignee: NanoGuard Technologies, LLC, St. Louis, MO (US)

( * ) Notice: Subject to any disclaimer, the term of this patent is extended or adjusted under 35 U.S.C. 154(b) by 360 days.

(21) Appl. No.: 17/017,517

(22) Filed: Sep. 10, 2020

(65) Prior Publication Data

US 2021/0308309 A1 Oct. 7, 2021

Related U.S. Application Data

(60) Provisional application No. 63/005,094, filed on Apr. 3, 2020.

(51) Int. Cl.
*A61L 2/20* (2006.01)
*A61L 2/00* (2006.01)
*A61L 2/26* (2006.01)
*C01B 13/11* (2006.01)
*A61L 101/02* (2006.01)

(52) U.S. Cl.
CPC ............. *A61L 2/202* (2013.01); *A61L 2/0094* (2013.01); *A61L 2/26* (2013.01); *C01B 13/11* (2013.01); *A61L 2101/02* (2020.08); *A61L 2202/11* (2013.01); *A61L 2202/24* (2013.01); *A61L 2202/25* (2013.01)

(58) Field of Classification Search
CPC .......... A61L 2/202; A61L 2/26; A61L 2/0094; A61L 2202/11; A61L 2202/24; A61L 2202/25; C01B 13/11
See application file for complete search history.

(56) References Cited

U.S. PATENT DOCUMENTS

| | | | |
|---|---|---|---|
| 2,837,666 | A | 6/1958 | Linder |
| 3,891,561 | A | 6/1975 | Lowther |
| 4,524,080 | A | 6/1985 | Sugisawa et al. |
| 4,643,876 | A | 2/1987 | Jacobs et al. |
| 5,184,046 | A | 2/1993 | Campbell |

(Continued)

FOREIGN PATENT DOCUMENTS

| | | |
|---|---|---|
| CA | 2 685 738 | 5/2010 |
| CN | 108 310 425 | 7/2018 |

(Continued)

OTHER PUBLICATIONS

U.S. Appl. No. 17/200,346, filed Mar. 12, 2021.

(Continued)

*Primary Examiner* — Sean E Conley
(74) *Attorney, Agent, or Firm* — EVAN LAW GROUP LLC

(57) ABSTRACT

A method of disinfecting a surface that is contaminated with a virus or suspected of contamination with a virus, including: producing a reactive gas by forming a high-voltage cold plasma (HVCP) from a working gas with a dielectric barrier discharge (DBD) system at a voltage of 20 kV to 150 kV; transporting the reactive gas at least 1 meter away from the HVCP; followed by contacting the surface with the reactive gas.

20 Claims, 25 Drawing Sheets

(56) References Cited

U.S. PATENT DOCUMENTS

| | | |
|---|---|---|
| 5,482,684 A | 1/1996 | Martens et al. |
| 5,656,238 A | 8/1997 | Spencer et al. |
| 5,895,587 A | 4/1999 | Sorensen |
| 6,007,770 A | 12/1999 | Peiper et al. |
| 6,093,432 A | 7/2000 | Mittal et al. |
| 6,096,564 A | 8/2000 | Denes et al. |
| 6,171,450 B1 | 1/2001 | Behnisch et al. |
| 6,331,514 B1 * | 12/2001 | Wurzburger ............ A61K 33/26 134/41 |
| 6,403,029 B1 | 6/2002 | Schmidt |
| 6,406,759 B1 | 6/2002 | Roth |
| 6,543,460 B1 | 4/2003 | Denes et al. |
| 6,638,475 B1 | 10/2003 | Lagunas-Solar et al. |
| 6,667,007 B1 | 12/2003 | Schmidt |
| 6,991,768 B2 | 1/2006 | Keras et al. |
| 7,101,518 B1 | 9/2006 | Ko |
| 8,097,217 B2 | 1/2012 | Song |
| 8,343,422 B2 | 1/2013 | Sato et al. |
| 8,372,460 B2 | 2/2013 | Meyers et al. |
| 8,475,712 B2 | 7/2013 | Henriksson |
| 8,475,723 B2 | 7/2013 | Keras |
| 8,545,764 B2 | 10/2013 | Gesche |
| 8,551,546 B2 | 10/2013 | Rasanayagam et al. |
| 8,557,187 B2 | 10/2013 | Ehlbeck et al. |
| 8,641,977 B2 | 2/2014 | Snowball |
| 8,771,595 B2 | 7/2014 | Paskalov |
| 8,834,803 B2 | 9/2014 | Sunderland |
| 8,865,085 B2 | 10/2014 | Nam et al. |
| 8,871,145 B2 | 10/2014 | Paskalov |
| 8,920,740 B2 | 12/2014 | Yang et al. |
| 8,961,894 B2 | 2/2015 | Keener et al. |
| 8,980,190 B2 | 3/2015 | Diver et al. |
| 9,067,788 B1 | 6/2015 | Spielman et al. |
| 9,114,373 B2 | 8/2015 | Misawa et al. |
| 9,220,162 B2 | 12/2015 | Takenoshita et al. |
| 9,295,280 B2 | 3/2016 | Jacofsky et al. |
| 9,363,880 B2 | 6/2016 | Keener et al. |
| 9,408,930 B2 | 8/2016 | Keener et al. |
| 9,539,352 B2 | 1/2017 | Keener et al. |
| 9,597,422 B2 | 3/2017 | Snowball |
| 10,194,672 B2 | 2/2019 | Keener et al. |
| 10,925,144 B2 | 2/2021 | Hochwalt |
| 11,000,045 B2 | 5/2021 | Keener et al. |
| 2002/0070127 A1 | 6/2002 | Song |
| 2002/0129902 A1 | 9/2002 | Babayan et al. |
| 2002/0153241 A1 | 10/2002 | Niv et al. |
| 2002/0175068 A1 | 11/2002 | Hammerstrom et al. |
| 2002/0182101 A1 | 12/2002 | Koulik et al. |
| 2003/0026877 A1 | 2/2003 | Ruan et al. |
| 2003/0030374 A1 | 2/2003 | Pai |
| 2003/0039726 A1 | 2/2003 | Yuan |
| 2003/0164285 A1 | 9/2003 | Korenev |
| 2003/0168009 A1 | 9/2003 | Denes |
| 2004/0001773 A1 | 1/2004 | Schmidt |
| 2004/0037736 A1 | 2/2004 | Perruchot et al. |
| 2004/0047762 A1 | 3/2004 | Masaoka et al. |
| 2004/0050682 A1 | 3/2004 | Paskalov et al. |
| 2004/0076543 A1 | 4/2004 | Sokolowski et al. |
| 2004/0131496 A1 | 7/2004 | Goetzelmann et al. |
| 2004/0141278 A1 | 7/2004 | Grosse et al. |
| 2004/0208804 A1 | 10/2004 | Hall et al. |
| 2004/0216845 A1 | 11/2004 | Golkowski |
| 2004/0250688 A1 | 12/2004 | Farkas et al. |
| 2005/0019209 A1 | 1/2005 | Burger et al. |
| 2005/0023128 A1 | 2/2005 | Keras |
| 2005/0056596 A1 | 3/2005 | Paskalov et al. |
| 2005/0109739 A1 | 5/2005 | Destrez et al. |
| 2005/0127843 A1 | 6/2005 | Koulik et al. |
| 2005/0189302 A1 * | 9/2005 | Latino .................. A61H 33/14 210/739 |
| 2005/0196315 A1 | 9/2005 | Babko-Malyi et al. |
| 2005/0274122 A1 | 12/2005 | Chang et al. |
| 2006/0027539 A1 | 2/2006 | Golkowski |
| 2006/0060464 A1 | 3/2006 | Chang |
| 2006/0137212 A1 | 6/2006 | Nomine |
| 2006/0193816 A1 * | 8/2006 | Elfersy .................. A01N 33/12 424/70.28 |
| 2006/0251550 A1 | 11/2006 | Keras |
| 2007/0020159 A1 | 1/2007 | Tsui |
| 2007/0104610 A1 | 5/2007 | Houston et al. |
| 2007/0261555 A1 | 11/2007 | Aubert |
| 2007/0270833 A1 | 11/2007 | Bonutti et al. |
| 2008/0006536 A1 | 1/2008 | Cuomo et al. |
| 2008/0063559 A1 | 3/2008 | Alexander et al. |
| 2008/0099406 A1 | 5/2008 | Ruan et al. |
| 2008/0173621 A1 | 7/2008 | Kuo |
| 2008/0193330 A1 | 8/2008 | Hotta et al. |
| 2008/0258648 A1 | 10/2008 | Bleukx et al. |
| 2008/0260578 A1 | 10/2008 | Engemann et al. |
| 2008/0292497 A1 | 11/2008 | Vangeneugden et al. |
| 2008/0314243 A1 | 12/2008 | Chan et al. |
| 2009/0121637 A1 | 5/2009 | Laroussi |
| 2009/0159461 A1 | 6/2009 | McCutchen et al. |
| 2009/0274592 A1 | 11/2009 | Bergeron |
| 2009/0288559 A1 | 11/2009 | Kuo |
| 2009/0297409 A1 | 12/2009 | Buchanan et al. |
| 2009/0304562 A1 | 12/2009 | Hayashi et al. |
| 2010/0006121 A1 | 1/2010 | Baxter et al. |
| 2010/0032285 A1 | 2/2010 | Thomas et al. |
| 2010/0119670 A1 | 5/2010 | Mazzariello |
| 2010/0206232 A1 | 8/2010 | Duclos et al. |
| 2010/0209293 A1 | 8/2010 | Ikawa et al. |
| 2010/0304146 A1 | 12/2010 | Krebs et al. |
| 2011/0014330 A1 | 1/2011 | Meyers et al. |
| 2011/0081273 A1 * | 4/2011 | Sunderland ............ A61L 9/22 422/108 |
| 2011/0115415 A1 | 5/2011 | Hong |
| 2011/0116967 A1 | 5/2011 | Roy et al. |
| 2011/0251604 A1 | 10/2011 | Staack et al. |
| 2011/0268850 A1 | 11/2011 | Rasanayagam et al. |
| 2012/0000782 A1 | 1/2012 | Hong |
| 2012/0093687 A1 | 4/2012 | Snowball |
| 2012/0156093 A1 | 6/2012 | Kitano |
| 2012/0156340 A1 | 6/2012 | Rasanayagam et al. |
| 2012/0156341 A1 | 6/2012 | Rasanayagam et al. |
| 2012/0183437 A1 | 7/2012 | Keener et al. |
| 2012/0213664 A1 | 8/2012 | Diver et al. |
| 2013/0053761 A1 | 2/2013 | Morfill et al. |
| 2013/0104742 A1 | 5/2013 | Deo et al. |
| 2013/0105025 A1 | 5/2013 | Fehr et al. |
| 2013/0164173 A1 | 6/2013 | Norris |
| 2013/0189156 A1 | 7/2013 | Keener et al. |
| 2013/0196099 A1 | 8/2013 | Sakamoto et al. |
| 2013/0319460 A1 | 12/2013 | Schneider et al. |
| 2013/0345620 A1 | 12/2013 | Zemel |
| 2014/0044595 A1 | 2/2014 | Keener et al. |
| 2015/0150297 A1 | 6/2015 | Kim et al. |
| 2015/0273094 A1 | 10/2015 | Keener et al. |
| 2015/0327430 A1 | 11/2015 | Dong et al. |
| 2015/0327562 A1 | 11/2015 | Zwijack |
| 2015/0342397 A1 | 12/2015 | Deo et al. |
| 2015/0373923 A1 | 12/2015 | Ferrell et al. |
| 2016/0174557 A1 | 6/2016 | Olesinski |
| 2016/0262410 A1 | 9/2016 | Hoefnagels |
| 2017/0000167 A1 | 1/2017 | Corrigan |
| 2017/0112157 A1 | 4/2017 | Keener et al. |
| 2017/0133205 A1 | 5/2017 | Ehlbeck et al. |
| 2018/0282715 A1 | 10/2018 | Carter |
| 2019/0159471 A1 | 5/2019 | Keener et al. |
| 2020/0396819 A1 | 12/2020 | Hochwalt |
| 2021/0219411 A1 | 7/2021 | Hochwalt |
| 2021/0267225 A1 | 9/2021 | Keener et al. |
| 2021/0308309 A1 | 10/2021 | Hochwalt |

FOREIGN PATENT DOCUMENTS

| | | |
|---|---|---|
| DE | 10 2014 107805 | 1/2015 |
| EP | 1 884 248 | 2/2008 |
| EP | 2 051 743 | 4/2009 |
| EP | 2 374 753 | 10/2011 |
| EP | 3 213 773 | 9/2017 |
| EP | 3 383 144 | 3/2018 |
| EP | 3 581 209 | 12/2019 |
| EP | 3 751 596 | 12/2020 |

(56) References Cited

FOREIGN PATENT DOCUMENTS

| | | |
|---|---|---|
| RU | 2102084 | 1/1998 |
| RU | 2199349 | 2/2003 |
| RU | 2254143 | 6/2005 |
| WO | 1997/18343 | 5/1997 |
| WO | 1997/022369 | 6/1997 |
| WO | 1998/51608 | 11/1998 |
| WO | 1998/51609 | 11/1998 |
| WO | 2002/022447 | 4/2000 |
| WO | 2000/054819 | 9/2000 |
| WO | 2002/078749 | 10/2002 |
| WO | 2006/004399 | 1/2006 |
| WO | 2007/067924 | 6/2007 |
| WO | 2007/124910 | 11/2007 |
| WO | 2007/124945 | 11/2007 |
| WO | 2008/072170 | 6/2008 |
| WO | 2008/096292 | 8/2008 |
| WO | 2008/126068 | 10/2008 |
| WO | 2008/127135 | 10/2008 |
| WO | 2008/144499 | 11/2008 |
| WO | 2009/040130 | 4/2009 |
| WO | 2009/041861 | 4/2009 |
| WO | 2009/098662 | 8/2009 |
| WO | 2011/116984 | 9/2011 |
| WO | 2011/123512 | 10/2011 |
| WO | 2012/038669 | 3/2012 |
| WO | 2012/079858 | 6/2012 |
| WO | 2012/097987 | 7/2012 |
| WO | 2012/112042 | 8/2012 |
| WO | 2012/113568 | 8/2012 |
| WO | 2012/125435 | 9/2012 |
| WO | 2012/130197 | 10/2012 |
| WO | 2013/076102 | 5/2013 |
| WO | 2013/076458 | 5/2013 |
| WO | 2014/135254 | 9/2014 |
| WO | 2014/152169 | 9/2014 |
| WO | 2015/091221 | 6/2015 |
| WO | 2016/007000 | 1/2016 |
| WO | 2016/140447 | 9/2016 |
| WO | 2017/019621 | 2/2017 |
| WO | 2017/070240 | 4/2017 |
| WO | 2018/045378 | 3/2018 |
| WO | 2020/251951 | 12/2020 |
| WO | 2021/202201 | 10/2021 |

OTHER PUBLICATIONS

U.S. Appl. No. 17/150,721, filed Jan. 15, 2021.
Jul. 11, 2017, U.S. Appl. No. 14/921,910, US.
Aug. 30, 2017, U.S. Appl. No. 14/921,910, US.
Oct. 18, 2017, U.S. Appl. No. 14/921,920, US.
Jan. 4, 2018, 16788620.9, EP.
Sep. 25, 2018, 16788620.9, EP.
Sep. 28, 2018, U.S. Appl. No. 14/921,910, US.
Feb. 1, 2019, 201610939647.X, CN.
Feb. 21, 2019, 16788620.9, EP.
Apr. 12, 2019, MX/a/2018/004893, MX.
Jun. 17, 2019, U.S. Pat. No. 3,039,902, CA.
Jul. 5, 2019, 201827013136, IN.
Jul. 25, 2019, 2018-520174, JP.
Aug. 26, 2019, 201610939647.X, CN.
Sep. 17, 2019, U.S. Appl. No. 16/215,187, US.
Sep. 19, 2019, 10-2018-7012556, KR.
Sep. 19, 2019, 19155626.5, EP.
Apr. 9, 2018, 16788620.9, EP.
Dec. 10, 2019, 10-2018-7012556, KR.
Dec. 6, 2019, 2018118775, RU.
Jan. 7, 2020, 2018-520174, JP.
Jan. 22, 2020, U.S. Appl. No. 16/215,187, US.
Jan. 21, 2020, 201610939647.X, CN.
Feb. 13, 2020, 19189770.1, EP.
Feb. 25, 2020, 19155626.5, EP.
Apr. 7, 2020, U.S. Appl. No. 16/442,380, US.
Apr. 1, 2020, 2018118775, RU.
Aug. 16, 2019, MX/a/2018/004893, MX.
Feb. 17, 2020, 10-2018-7012556, KR.
Aug. 21, 2020, U.S. Appl. No. 16/442,380, US.
Aug. 18, 2020, U.S. Appl. No. 16/215,187, US.
Oct. 15, 2020, U.S. Appl. No. 16/442,380, US.
Nov. 16, 2020, U.S. Appl. No. 16/215,187, US.
Jan. 12, 2021, U.S. Appl. No. 16/215,187, US.
Dec. 24, 2020, 202021402985.8, CN.
Jun. 17, 2021, 19155626.5, EP.
Mar. 30, 2022, 19189770.1, EP.
International Search Report dated Jan. 25, 2017 for PCT application No. PCT/U82016/057753, 12 pages.
Connolly, J. et al.. "Characterization and antimicrobial efficacy against *E. coli* of a helium/air plasma at atmospheric pressure created in a plastic package", Journal of Physics D: Applied Physics. vol. 46. No. 3. pp. 1-12, (2013).
Misra. N.N. et al., "In-package atmospheric pressure cold plasma treatment of cherry tomatoes", Journal of Bioscience and Bioengineering, vol. 118, No. 2, pp. 177-182, (2014).
Chiper. A.S. et al., "Atmospheric pressure plasma produced inside a closed package by a dielectric barrier discharge in $Ar/CO_2$ for bacterial inactivation of biological samples", Plasma Sources Science and Technology, vol. 20, No. 2, pp. 1-10, (2011).
Kolb, J.F. et al., "Cold atmospheric pressure air plasma jet for medical applications", Applied Physics Letters, vol. 92, pp. 241501-1-241501-3, (2008).
Winter, J. et al., "Aspects of Uv-absorption spectroscopy on ozone in effluents of plasma jets operated in air", Journal of Physics D: Applied Physics, vol. 45, pp. 1-7, (2012).
Katsonis, K. et al., "Global modeling of $N_2O$ discharges: Rate coefficients and comparison with ICP and glow discharges results", International Journal of Aerospace Engineering, vol. 2013, pp. 1-25, (2013).
"Aflatoxin", Wikipedia, pp. 1-5, found at https://en.wikipedia.org/wiki/Aflatoxin, printed on Jul. 10, 2015.
Lunov, O. et al., "Cell death induced by ozone and various nonthermal plasmas: therapeutic perspectives and limitations", Scientific Reports, vol. 4, pp. 1-11, (2014).
"Volt", Wikipedia, pp. 1-4, found at https://en.wikipedia.org/wiki/Volt, Printed on Jul. 10, 2015.
Moiseev, T. et al., "Post-discharge gas composition of a large-gap DBD in humid air by UV-Vis absorption spectroscopy", Plasma Sources Science and Technology, vol. 23, pp. 1-13, (2014).
"Endospore", Wikipedia, pp. 1-6, found at https://en.wikipedia.org/wiki/Endospore, Printed on Sep. 10, 2017.
Trombete, FM. et al., "Efficacy of ozone treatment on mycotoxins and fungal reduction in artificially contaminated soft wheat grains", Journal of Food Processing and Preservation, vol. 41, No. 3, (2017). Abstract Only.
McKenzie, K.S. et al., "Oxidative degradation and detoxification of mycotoxins using a novel source of ozone", Food and Chemical Toxicology, vol. 35, No. 8, pp. 807-820, (1997). Abstract Only.
Wang L. et al., "Effect of ozone treatment on deoxynivalenol and wheat quality", PLoS One, vol. 11, No. 1, pp. 1-13, (2016).
McDonough, M.X. et al., "Ozone application in a modified screw conveyor to treat grain for insect pests, fungal contaminants, and mycotoxins", Journal of Stored Products Research, vol. 47, No. 3, pp. 249-254, (2011).
Tiwari, B.K. et al., "Application of ozone in grain processing", Journal of Cereal Science, vol. 51, issue 3, pp. 248-255, (2010). Abstract Only.
Guzel-Seydima, Z.B. et al., "Use of ozone in the food industry", LWT-Food Science and Technology, vol. 37, No. 4, pp. 453-460, (2004).
"Listeria monocytogenes", Wikipedia, pp. 1-7, found at https://en.wikipedia.org/wiki/Listeria_monocytogenes, printed on Jul. 10, 2015.
"Bacillus atrophaeus", Wikipedia, pp. 1-2, found at https://en.wikipedia.org/wiki/Bacillus_atrophaeus, printed on Jul. 10, 2015.
"*Salmonella enterica*", Wikipedia, pp. 1-3, found at https://en.wikipedia.org/wiki/Salmonella_enterica, printed on Jul. 10, 2015.
"Clostridium botulinum", Wikipedia, pp. 1-6, found at https://en.wikipedia.org/wiki/Clostridium_botulinum, printed on Jul. 10, 2015.

(56) References Cited

OTHER PUBLICATIONS

"Sterilization (microbiology)", Wikipedia, pp. 1-10, found at https://en.wikipedia.org/wiki/Sterilization_(microbiology), printed on Jul. 10, 2015.

Food and Drug Administration, "Guidance for industry for the submission documentation for sterilization process validation in applications for human and veterinary drug products", Office of Training and Communication Division of Drug Information, CDER, FDA, pp. 1-18, (1994).

Chaven, S. et al., "Food safety systems for low-acid aseptic beverages", Food Safety Magazine, pp. 1-6, found at www.foodsafetymagazine.com/magazine-archive1fjunejuly-2012/food-safety-systems-for-low-acid-aseptic-beverages/, (2012).

U.S. Food and Drug Administration, "Guidance for Industry: Juice HACCP hazards and controls guidance first edition: Final guidance", pp. 1-67, (2004).

Lopez, J.L., "Dielectric barrier discharge, ozone generation, and their applications", Complex Plasmas Summer Institute, pp. 1-93, (2008).

Pankaj, S.K. et al., "Degradation kinetics of organic dyes in water by high voltage atmospheric air and modified air cold plasma", Water Science & Technology, pp. 1-8, (2017).

Pankaj, S.K. et al., "Effect of high voltage atmospheric cold plasma on white grape juice quality", Journal of the Science of Food and Agriculture, vol. 97, pp. 4016-4021, (2017).

Yepez, X.V. et al., "High-voltage atmospheric cold plasma (HVACP) hydrogenation of soybean oil without trans-fatty acids", Innovative Food Science and Emerging Technologies, vol. 38, pp. 169-174, (2016).

Wan, Z. et al., "High voltage atmospheric cold plasma treatment of refrigerated chicken eggs for control of *Salmonella enteritidis* contamination on egg shell", LWT—Food Science and Technology, vol. 76, pp. 124-130, (2017).

Xu, L. et al., "Microbial inactivation and quality changes in orange juice treated by high voltage atmospheric cold plasma", Food Bioprocess Technology, vol. 10, pp. 1778-1791, (2017).

McClurkin-Moore, J.D. et al., "The effect of high-voltage atmospheric cold plasma treatment on the shelf-life of distillers wet grains", Food Bioprocess Technology, vol. 10, pp. 1431-1440, (2017).

Pankaj, S.K. et al., "Cold plasma: background, applications and current trends", Current Opinion in Food Science, vol. 16, pp. 49-52, (2017).

Shi, H. et al., "Reduction of aflatoxin in corn by high viltage atmospheric cold plasma", Food Bioprocess Technology, vol. 10, pp. 1042-1052, (2017).

Misra, N.N. et al., "The effects of nonthermal plasma on chemical quality of strawberries", Postharvest Biology and Technology, vol. 110, pp. 197-202, (2015).

Hojnik, N. et al., "Mycotoxin decontamination of food: Cold atmospheric pressure plasma versus "classic" decontamination", Toxins, vol. 9, No. 151, pp. 1-19, (2017).

Siciliano, I. et al., "Use of cold atmospheric plasma to detoxify hazelnuts from aflatoxins", Toxins, vol. 8, No. 125, pp. 1-10, (2016).

Ma, H. et al., "Non-thermal pasteurization of liquid foods using non-thermal plasma", Transactions of the CSAE, vol. 18, No. 5, pp. 155-159, (2002).

Li, Y. et al., "Degradation of aflatoxin B1 in agricultural products by low temperature radio frequency plasma", Science and Technology of Cereals, Oils and Foods, vol. 22.5, pp. 1-11, (2014).

Chen, Y., "High voltage atmospheric cold plasma treatment of refrigerated chicken eggs for control of *Salmonella enteritidis* on external surfaces", Purdue University, Theses and Dissertations, pp. 1-209, (2014).

Morrill, G.E. et al., "Nosocomial infections—a new approach towards preventive medicine using plasmas", New Journal of Physics, vol. 11, 115019, pp. 1-10, (2009).

Lu, H. et al., "Bacterial inactivation by high-voltage atmospheric cold plasma: influence of process parameters and effects on cell leakage and DNA", Journal of Applied Microbiology, vol. 116, pp. 784-794, (2013).

Lopez, M. et al., "A review on non-thermal atmospheric plasma for food preservation: Mode of action, determinants of effectiveness, and applications", Frontiers in Microbiology, vol. 10, pp. 1-21, (2019).

Extended European Search Report dated Feb. 25, 2020 for European application No. 19155626.5, 8 pages.

"Ozone effects on pathogens", Ozone Solutions, 5 pages, downloaded on Mar. 13, 2020, found at www.ozonesolutions.com/blog/ozone-effects-on-pathogens-bc5a25/.

"Ozone as a disinfectant to destroy pathogens, like the coronavirus", Ozone Solutions, 2 pages, downloaded on Mar. 13, 2020, found at www.ozonesolutions.com/blog/ozone-as-a-disinfectant-to-destroy-pathogens-like-the-coronavirus/.

Foarde, K. et al., "Ozone antimicrobial efficacy", U.S. Environmental Protection Agency, National Risk Management Research Laboratory, pp. 1-13, (2007).

Pradeep, P. et al., "Non-thermal plasmas (NTPs) for inactivation of viruses in abiotic environment", Research Journal of Biotechnology, vol. 11, No. 6, pp. 91-96, (2016).

Wu, Y. et al., "MS2 virus inactivation by atmospheric-pressure cold plasma using different gas carriers and power levels", Applied and Environmental Microbiology, vol. 81, No. 3, pp. 996-1002, (2015).

Yasuda, H. et al., "Biological evaluation of DNA damage in bacteriophages inactivated by atmospheric pressure cold plasma", Plasma Processes and Polymers, vol. 7, pp. 301-308, (2010).

Alshraiedeh, N.H. et al., "Atmospheric pressure, nonthermal plasma inactivation of MS2 bacteriophage: effect of oxygen concentration on virucidal activity", Journal of Applied Microbiology, vol. 115, pp. 1420-1426, (2013).

Bae, S.C. et al., "Inactivation of murine norovirus-1 and hepatitis a virus on fresh meats by atmospheric pressure jets", Food Research International, vol. 76, pp. 342-347, (2015).

Cowling, B.J. et al., "Aerosol transmission is an important mode of influenza A virus spread", Nature Communications, vol. 4, 1935, pp. 1-6, (2013).

Kuzmanovic, D.A. et al., "Bacteriophage MS2: Molecular weight and spatial distribution of the protein and RNA components by small-angle neutron scattering and virus counting", Structure, vol. 11, pp. 1339-1348, (2003).

Wolf, C. et al., "Proxies to monitor the inactivation of viruses by ozone in surface water and wastewater effluent", Water Research, vol. 166, (2019).

Brie, A. et al., "Inactivation of murine norovirus and hepatitis A virus on fresh raspberries by gaseous ozone treatment", Food Microbiology, vol. 70, pp. 1-6, (2018).

Hudson, J.B. et al., "Development of a practical method for using ozone gas as a virus decontaminating agent", Ozone: Science & Engineering, vol. 31, No. 3, pp. 216-223, (2009).

Muller, J.A. et al., "Development of a high-throughput colorimetric Zika virus Infection Assay", Medical Microbiology and Immunology, vol. 206, issue 2, pp. 175-185, (2017).

World Health Organization, "Zika virus Situation Report—5th. Feb. 2016", 6 pages, (2016).

Rasmussen, S.A. et al., "Zika virus and birth defects—reviewing the evidence for causality", The New England Journal of Medicine, pp. 1-7, (2016).

Muller, J.A. et al., "Inactivation and environmental stability of Zika virus", Emerging Infectious Diseases, vol. 22, No. 9, pp. 1685-1687, (2016).

Aubry, M. et al., "Inactivation of Zika virus in plasma with amotosalen and ultraviolet a illumination", Transfusion, vol. 56, pp. 33-40, (2016).

Butot, S. et al., "Procedure for rapid concentration and detection of enteric viruses from berries and vegetables", Applied and Environmental Microbiology, vol. 73, No. 1, pp. 186-192, (2007).

Woolston, J. et al., "Bacteriophage lytic for salmonella rapidly reduce salmonella contamination on glass and stainless-steel surfaces", Bacteriophage, vol. 3, issue 3, pp. e25697-1-.e25697-6, (2013).

(56) References Cited

OTHER PUBLICATIONS

Carey-Smith, G.V. et al., "Isolation and characterization of bacteriophages infecting *Salmonella* spp.", Fems Microbiology Letters, vol. 258, pp. 182-186, (2006).
Soffer, N. et al., "Bacteriophages safely reduce salmonella contamination in pet food and raw pet food ingredients", Bacteriophage, vol. 6, No. 3, pp. e1220347-1-e1220347-8, (2016).
Shin, H. et al., "Receptor diversity and host interaction of bacteriophages infecting salmonella enterica serovar typhimurium", Plos One, vol. 7, issue 8, pp. e43392-1-e43392-11, (2012).
"Influenza type a viruses—Avian influenza (Flu)", Centers for Disease Control and Prevention, 2 pages, found at www.cdc.gov/flu/avianflu/influenza-a-virus-subtypes.htm, (2020).
Dow Corning, Product Information, "Dow Corning® 3-4207 Dielectric Tough Gel", 3 pages, (2017).
Cock, I. et al., "A modified MS2 bacteriophage plaque reduction assay for the rapid screening of antiviral plant extracts", Pharmacognosy Research, vol. 2, issue 4, pp. 221-228, (2010).
ACL Inc., Product Information, "8690 Staticide Acrylic Conformal Coating", 1 page, (2016).
Corning Gorilla Glass, Product Information, "Corning Gorilla Glass 3", 2 pages, (2016).
ResinLab, an Ellsworth Adhesives Company, Product Information,. "Technical Data Sheet EP750 Clear", 3 pages, (2016).
ResinLab, an Ellsworth Adhesives Company, "Safety Data Sheet for EP750 Clear A", pp. 1-13, (2015).
ResinLab, an Ellsworth Adhesives Company, "Safety Data Sheet for EP750 Clear B", pp. 1-9, (2015).
Acculam Laminated Thermoset Plastic, Product Data Sheet, "Acculam® Epoxyglas G10, FR4", 1 page, (2017).
Encon2.3 Fact Sheet, "Improving energy efficiency in grain drying", 5 pages, (2012).
Biomin, "World Mycotoxin Survey, the global threat", 5 pages, (2019).
SciFinder Search Report on "Inactivation of Viruses using Ozone", pp. 1-14, generated on Feb. 10, 2020.
EPA, "Guidance to Registrants: Process for making claims against emerging viral pathogens not on EPA-registered disinfectant labels", Environmental Protection Agency, pp. 1-8, (2016).
International Search Report dated Oct. 27, 2020 for PCT application No. PCT/US2020/036833, 12 pages.
International Search Report and written opinion dated Oct. 28, 2021 for PCT application No. PCT/US2021/023941, 21 pages.
Extended European Search Report dated Feb. 2, 2023 for European application No. 22203129.6. 13 pages.
Oct. 4, 2022, U.S. Appl. No. 17/200,346, US.
Dec. 14, 2021, PCT/U82020/036833, WO.
Sep. 29, 2022, PCT/US2021/023941, WO.
Nov. 7, 2022, U.S. Appl. No. 17/017,517, U.
Dec. 15, 2022, 19189770.1, EP.
Nov. 22, 2022, 202010264719.1, CN.
Feb. 21, 2023, U.S. Appl. No. 17/150,721, US.
Mar. 14, 2023, 22203129.6, EP.
Jun. 15, 2023, U.S. Appl. No. 17/017,517, US.
Jul. 19, 2023, U.S. Appl. No. 17/200,346, US.
Aug. 7, 2023, 1955626.5, EP.
Jul. 31, 2023, 202010264719.1, CN.
Sep. 14, 2023, U.S. Appl. No. 17/200,346, US.
Sep. 22, 2023, U.S. Appl. No. 17/017,517, US.
Oct. 11, 2023, U.S. Appl. No. 17/017,17, US.
Oct. 17, 2023, U.S. Appl. No. 17/150,721, US.
Nov. 7, 2023, U.S. Appl. No. 17/150,721, US.
Nov. 20, 2023, 22203129.6, EP.

\* cited by examiner

METHODS OF DISARMING VIRUSES USING REACTIVE GAS

BACKGROUND

Biological decontamination and sterilization have a broad array of applications including medical equipment and device sterilization, food production and preservation, and preparation of consumer goods. Chemicals, heat, high-energy electron beams, and X-ray or gamma-ray irradiation systems are presently used for sterilization. Each of these systems has trade-offs due to the cost, efficiency, immobility, electric power requirements, toxic waste, personal hazard and the time required for sterilization or decontamination.

Plasmas have been used for decontamination and sterilization. Plasma, a fourth state of matter distinguished from gas, liquid and solid, may be produced through electrical discharge, for example electrical discharge through a gas. Although all plasmas contain electrons, ions and neutral species, they will have different properties depending on the composition of the gas used to prepare the plasma, as well as the electrical and structural configuration of the device used to produce the plasma.

One type of plasma is high-voltage cold plasma (HVCP), which may be prepared using dielectric barrier discharge (DBD) systems. HVCP may be prepared through a non-equilibrium breakdown of a gas, using voltages preferably of 30 kV to 500 kV, typically at a frequency of 50 or 60 Hz with a DBD system. HVCP has not been studies as well as other types of plasmas, such as thermal plasma or RF plasmas. Consequently, there is presently no theory which explains the properties of these plasmas, nor the various excited and reactive species produced in such plasma. Over the last decade experimental examination of HVCP has been carried out to study this plasma.

Direct exposure of materials to HVCP has been studied. Of particular relevance are the studies exposing biological products and contaminants to HVCP, where the biological products are sealed inside packages and the HVCP is produced inside the package. In such studies, packaged foods such as produce and other materials were sterilized in a short period of time. The product inside the packages comes into direct contact with the plasma. Since the packages are sealed, reactive gas produced in the plasma remains in contact with the product until they decay back to their nascent state, is not diluted or dispersed, and the packaged product is protected from recontamination, dramatically extending the shelf life of the products, such as fruits and vegetables. See, for example, U.S. Pat. Pub., Pub. Nos. 2013/0189156 and 2014/0044595, both to Keener et al.

Ozone gas has been recognized as a disinfectant, and ozone has been used to treat surfaces in order to remove odors, such as smoke odor. Ozone is capable of killing viruses. For example, ozone treatment is an integral part of many water and wastewater treatment facilities (Wolf, C., et al., "Proxies to monitor the inactivation of viruses by ozone in surface water and wastewater effluent", Water Research, Volume 166 (2019)). Ozone has also been used to treat products, such as fruit (Brie, A., et al., "Inactivation of murine norovirus and hepatitis A virus on fresh raspberries by gaseous ozone treatment", Food Microbiol., vol. 70, pg. 1-6 (2018)). These treatments make water and products safe for consumption.

The recent emergence of various viral diseases combined with limited effective therapies, have created demand for development of potent disinfecting approaches and therapies that can address these viral diseases. Despite progress in controlling environmental and human virus pathogens through vaccination, new approaches are required to disinfect these emerging public health threats. Such techniques should be appropriate to disarm food-, air-, surfaces-, and water-borne viruses thus preventing their infection and spread among communities.

Some viruses may be spread through contact, large respiratory droplets and small particle droplet nuclei (aerosols), and even from contaminated surfaces. Experimental studies have demonstrated that influenza virus can remain infectious in small particle aerosols, and can transit across rooms (Cowling B J, et al., "Aerosol transmission is an important mode of influenza A virus spread." Nat Commun., 4, 1935 (2013)). Corona viruses and rotaviruses can spread by contact with a contaminated surface. Measles is similarly contagious.

Current techniques for disarming viruses that may be present on surfaces include spraying liquid disinfectant in order to disarm any virus that may be present. The people responsible for spraying the disinfectant must wear protective clothing, in order to protect themselves from infection or contamination.

Ozone has been used as a virus decontaminating agent (Hudson J B, et al., "Development of a Practical Method for Using Ozone Gas as a Virus Decontaminating Agent" Ozone: Science & Engineering, 31, 216 (2009)). Treatment of various surfaces to remove viruses was carried using 20-25 ppm ozone gas. Some decontamination was achieved under ambient conditions, but a much greater effect was achieved when the ozone gas was humidified to greater than 90% relative humidity. A prototype device is described containing 8 corona discharge units, a circulating fan, and a catalytic converter to convert ozone back to oxygen after the treatment.

SUMMARY

In a first aspect, the present invention is a method of disinfecting a surface suspected of contamination with a virus, including producing a reactive gas by forming a high-voltage cold plasma (HVCP) from a working gas with a dielectric barrier discharge (DBD) system at a voltage of 20 kV to 150 kV; transporting the reactive gas at least 1 meter away from the HVCP; followed by contacting the surface with the reactive gas to disinfect the surface. A host infected with the virus had contacted the surface.

In a second aspect, the present invention is a method of disinfecting a surface contaminated with a virus, including producing a reactive gas by forming a high-voltage cold plasma (HVCP) from a working gas with a dielectric barrier discharge (DBD) system at a voltage of 20 kV to 150 kV; transporting the reactive gas at least 1 meter away from the HVCP; followed by contacting the surface with the reactive gas to disinfect the surface. A host infected with the virus had contacted the surface.

Definitions

All electrical potential described herein is specified as volts (V) and kilovolts (kV) root mean squared (RMS), and the power is derived from an alternating current. Percent (%) gas compositions are volume percent.

A cold plasma refers to plasma which has a temperature of at most 40° C. above the temperature of the gas used to prepare the plasma (that is, the working gas), more preferably a temperature of at most 20° C. above the temperature of the gas used to prepare the plasma.

High-voltage cold plasma (HVCP) means a cold plasma prepared using a dielectric barrier discharge (DBD) system, using voltages of at most 500 kV, with a frequency at most to 5000 Hz, prepared from a gas having a pressure of 10 to 50000 Torr, such as 760 Torr (atmospheric pressure). HVCP is not a thermal plasma, is not a microwave plasma and is not a radio frequency (RE) plasma. HVCP plasmas are generated under non-equilibrium breakdown conditions.

Reactive gas means the gas produced by an HVCP, including excited and chemically reactive species, but not those species which dissipate in 0.2 seconds or less. The composition of a reactive gas will change over time as excited species dissipate and chemical reactions within the reactive gas take place. Reactive gas is the gas that may be moved away from the DBD system that is producing an HVCP. A reactive species or excited species is considered to be present in a reactive gas if it can be detected using spectroscopy.

Dielectric barrier discharge (DBD), or a DBD system, means a system having at least two electrodes separated by a dielectric barrier, and may have more electrodes, where a dielectric barrier is present between each electrode, to prevent charge generated in the gas by a discharge from reaching an electrode. The shortest distance between adjacent electrodes in a DBD system is preferably at most 30 cm (or 12 inches), and preferably is at least 0.5 cm (or 0.25 inches). Preferably, DBD systems are configures to operate under conditions to produce an HVCP. Examples of DBD systems are illustrated in FIGS. 1A, 1B, 1C, 1D, 1E and 1F; preferably, the electrodes are spaced apart with a gap or plenum directly between the electrodes as illustrated in FIGS. 1A, 1B, 1C and 1F.

Working gas and working gas mixture refers to the gas which is used to form a plasma.

Package means a container having a volume of at most 6 gallons (or 22.7 liters).

Sealed or substantially sealed means that the gases inside the package or container remains inside and not flow or diffuse out of the package or container for at least 24 hours, if left undisturbed.

The term "disinfect" means that the virus has been destroyed and/or any virus present can no longer cause disease.

A "host" means a human, animal, or plant in which the virus causes disease or in bacteria, the virus causes lysis of the bacteria.

The phrase "a surface contaminated with a virus" means that a virus is present on a surface.

The phrase "a surface suspected of contamination" means that a host who is infected with the virus has contacted the surface.

The phrase "contacted a surface" includes physical contact, as well as exposing a surface to large respiratory droplets, small particle droplet nuclei (aerosols), or other shedding of virus.

In order to determine the effectiveness of a treatment to disinfect surfaces, the following protocol may be used. The protocol may be referred to as a "MS2 phage plaque assay test". This protocol may be used to validate the effectiveness of a treatment for reducing the amount of virus by providing MS2 phage samples as a proxy for other viruses, and treating the samples to measure the amount of MS2 phage reduction that resulted from the treatment. The protocol includes comparing the treated MS2 phage samples to untreated MS2 phage samples for use as a control. First, a solution containing the MS2 phage is spotted onto the surface of several sterile filter papers. The filter papers are allowed to dry and placed in a clean container at 4° C. prior to experimental treatment. Then the treated filter papers are treated with reactive gas (or other disinfectant treatment). The untreated filter papers are stored and not exposed to any treatment in order to serve as a control. After the treatment, the treated filter papers are placed into sterile plastic containers and transported in a chilled cooler to a laboratory for extraction using SM buffer (see Table 7, below, for the specific SM buffer formula). For extraction, the treated and untreated papers are aseptically sliced into 0.5 cm wide strips which are stacked and subsequently cut into 50 ml sterile tubes. SM buffer (5 mL) is added to each tube and extraction of the phage is performed over the course of 10 minutes. Just after the buffer is added and at each 2-minute interval during the 10 minutes, each sample is gently pulse-vortexed for 15 seconds. Thereafter, the tubes are centrifuged at 5000 rpm at 4° C. The supernatant containing residual phage is then filtered through 0.22 uM nylon syringe filters into 15 ml sterile tubes. This supernatant will be added to a host $E.$ $coli$ culture. Several dilutions of the treated and untreated filter papers extracts are made and the concentrations of recovered phage are determined by plaque assay using TSB top agar and bottom agar plates. It may be necessary to perform more dilutions to obtain a phage concentration that produces an appropriate number of plaques. 0.15 ml of the 3-hour bacterial culture is diluted 1:5 in TSB and is added to 3 ml of melted top/soft agar maintained at 42-45° C. by a water bath, followed by addition of 15 μl of diluted MS2 phage extract. The mixture is then vortexed gently, poured on bottom agar plates, and allowed to solidify. The plates are then incubated upside down, overnight in a 37° C. incubator. The following day, the formed plaques (clear areas) on the plates are counted and results tabulated. The $E.$ $coli$ culture is begun by inoculating 10 ml of TSB broth with 100 μl of $E.$ $coli$ suspension and growing the bacteria culture overnight in a 37° C. incubator. The following day, the overnight culture is used to start another fresh $E.$ $coli$ culture. 1 ml of the overnight culture is added to 9 ml of fresh TSB medium (1:10 dilution of overnight culture) and grown for 3 hours in the same conditions. This fresh culture is then diluted 1:5 in TSB medium and used as the bacteria hosts.

A 2-$\log_{10}$ reduction means that the amount of active virus that is present on a surface after treatment is $\frac{1}{100}^{th}$ of the amount of active virus that was present prior to the treatment, as determined by the MS2 plaque assay test; this test does not require that the virus of interest is actually present prior to treatment, but rather is a measure of the virus killing ability of the treatment. Similarly, an X-$\log_{10}$ reduction, where X is 3, 4, 5, or 6, means that the amount of active virus that is present on a surface after treatment is $\frac{1}{1000}$th, $\frac{1}{10,000}$th, $\frac{1}{100,000}$th and $\frac{1}{1,000,000}$th of the amount of virus that was present prior to the treatment, respectively.

BRIEF DESCRIPTION OF THE DRAWINGS

The following figures are provided to help illustrate the products, devices and methods of the application, but other variations and configurations are possible. The figures are not drawn to scale, with the size of some parts increased or decreased for clarity.

DETAILED DESCRIPTION

Figure 1A:
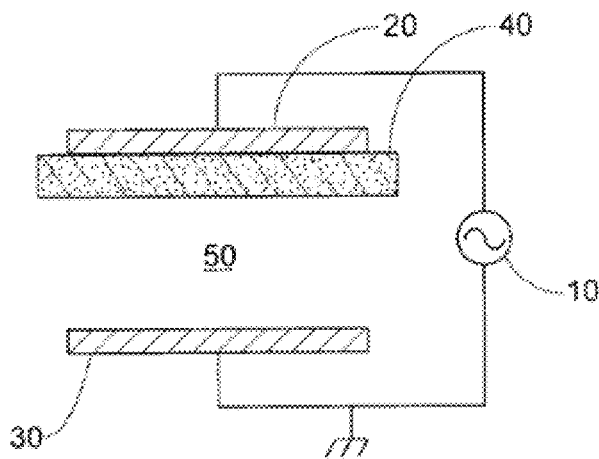
FIGS. 1A, 1B, 1C, 1D, 1E and 1F are schematic illustrations of a variety of DBD systems.
Figure 1B:
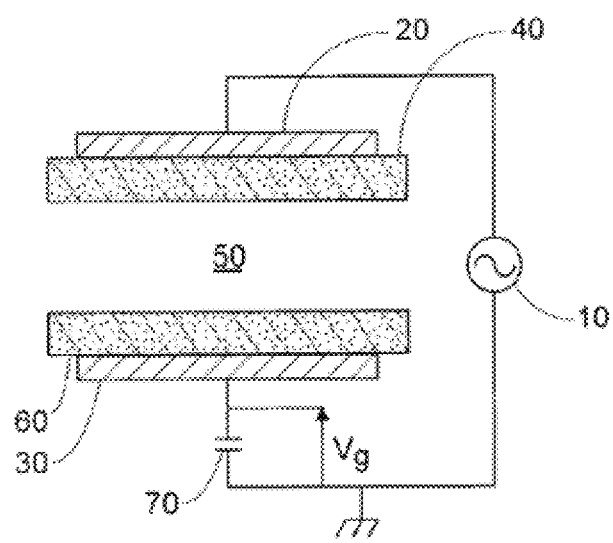
Figure 1C:
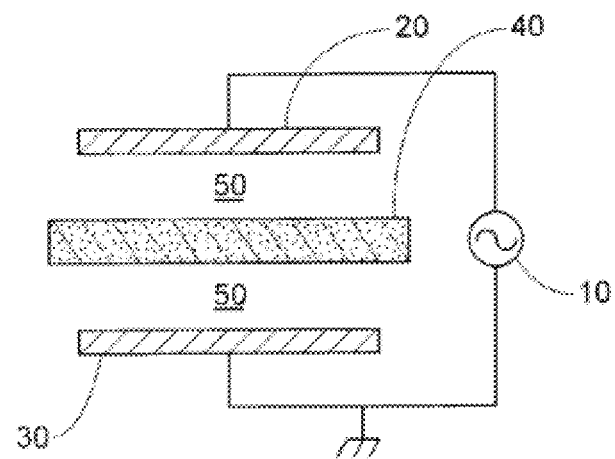
Figure 1D:
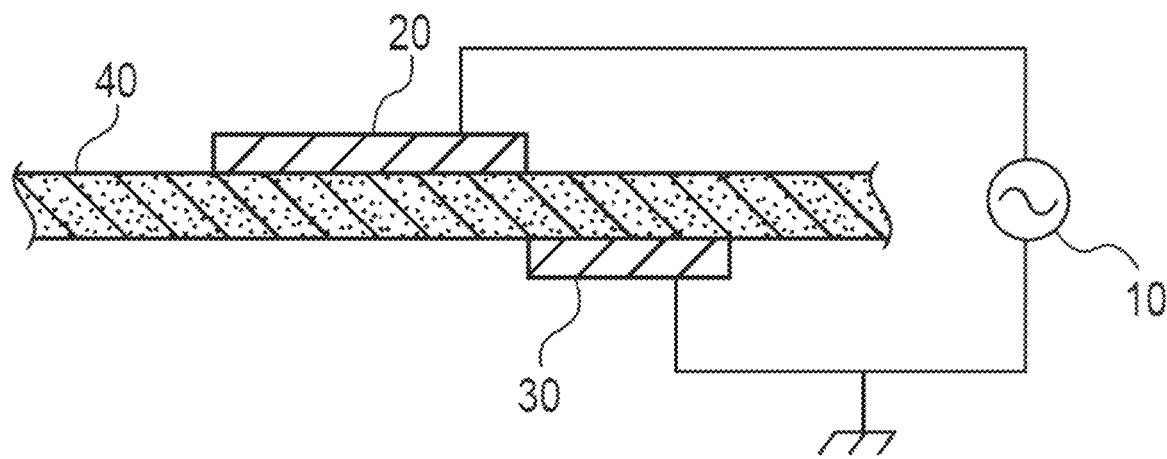
Figure 1E:
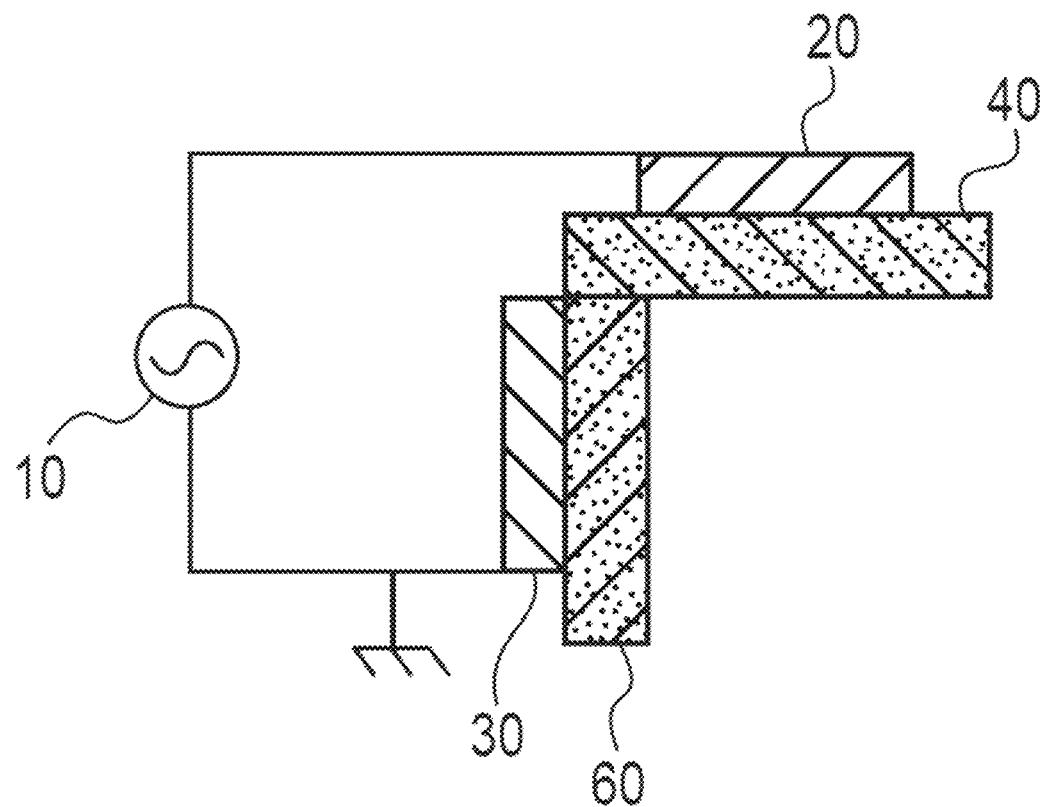
Figure 1F:
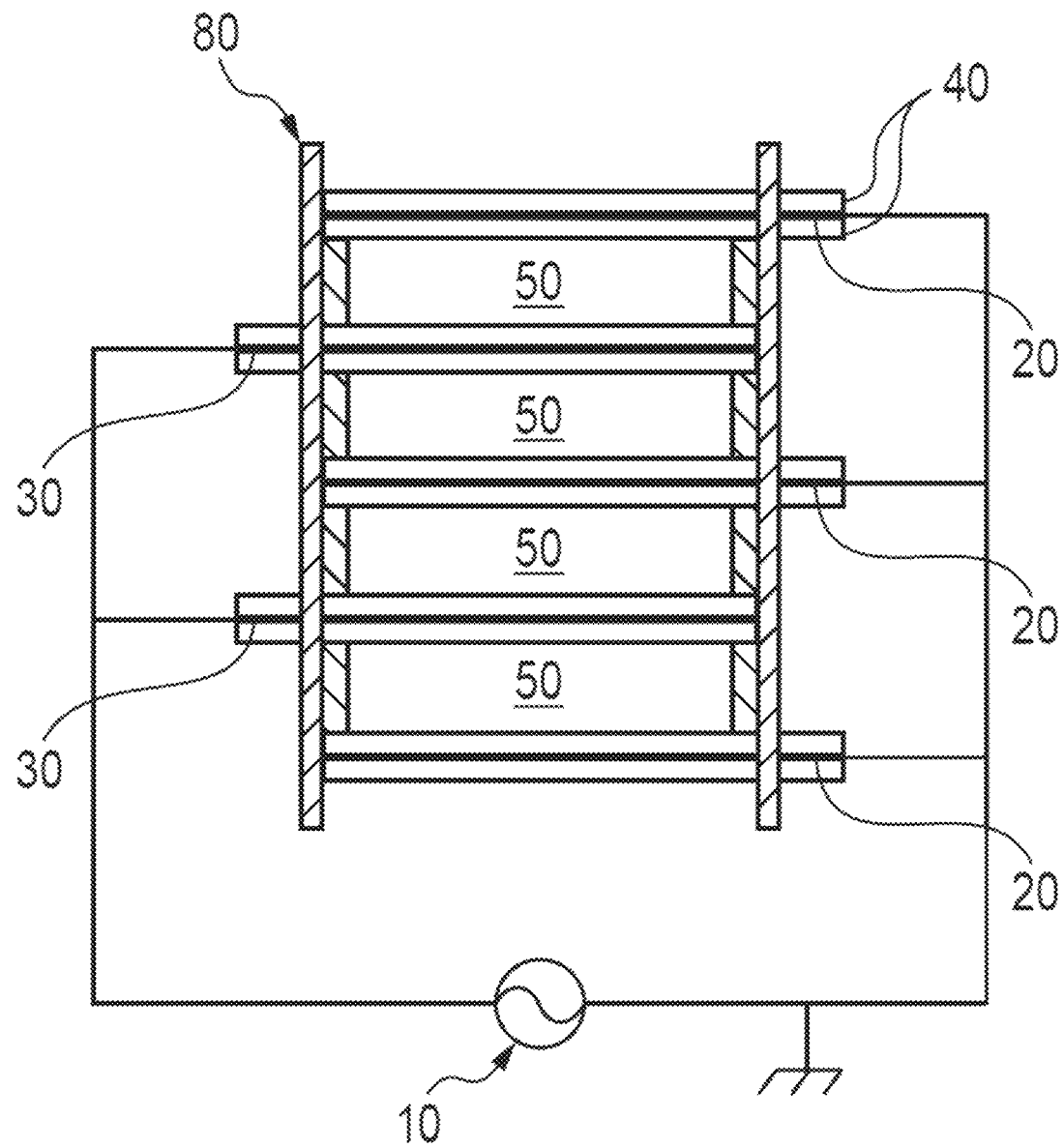

The present invention makes use of reactive gas produced by HVCP. The reactive gas is able to disinfect surfaces even when transported a significant distance from the DBD system where the plasma is produced, for example 3 to 30 meters (or 10 to 100 feet). Furthermore, the reactive gas is able to disarm viruses. This is quite surprising, because unlike HVCP produced within a package, there is no direct exposure of the product to the HVCP, the contact time of the reactive gas with the product is limited, for example for 1 second, 1 minute, 30 minutes, or one hour. Preferably, the plasma does not contact the surface. Furthermore, because the reactive gas is transported away from the DBD system where the HVCP is produced, it is diluted by both diffusion into the surrounding gas, and mixed with the surrounding gas and/or the working gas. Since the reactive gas is transported away from the DBD system, larger surfaces may be treated. In addition, large scale disinfection, such as disinfection of a vehicle or room may also be carried out. Furthermore, the effectiveness of the reactive gas is expected to be greater than what would be expected from the ozone content alone.

The Environmental Protection Agency (EPA) and the Centers for Disease Control and Prevention (CDC) recognize that viruses can be ranked with respect to their tolerance to disinfectants (EPA, "Guidance to Registrants: Process for Making Claims Against Emerging Viral Pathogens Not on EPA-Registered Disinfectant Labels", published on Aug. 19, 2016). With this approach, viruses are divided into three subgroups: small non-enveloped, large non-enveloped and enveloped viruses. According the hierarchy, if a disinfectant can kill a small non-enveloped virus it should be able to kill any large non-enveloped virus and any enveloped virus. Similarly, a disinfectant that can kill a large, non-enveloped virus can kill any enveloped virus. The reactive gas of the present application kills MS2 phage virus, as shown by Examples 1 and 4. MS2 phage is a small, non-enveloped virus. As killing this virus is the most challenging, the reactive gas would be expected to also kill any virus from the other subgroups. This expectation is borne out by the killing of the zika virus and *Salmonella enterica* bacteriophage, as shown in Examples 2 and 3 respectively. Similarly, coronaviruses are classified as an enveloped virus, so the reactive gas would be expected to kill coronavirus and disinfect a surface, if coronavirus was present prior to treatment with the reactive gas.

When the reactive gas contacts a surface, it disinfects the surface, if virus is present. The reduction may be at least a 2-$\log_{10}$ reduction, a 3-$\log_{10}$ reduction, a 4-$\log_{10}$ reduction, 5-$\log_{10}$ reduction, or a 6-$\log_{10}$ reduction in the activity of the virus. The MS2 phage plaque assay test may be used to determine the effectiveness of the disinfection. This test does not require that the virus of interest is actually present prior to treatment, but rather is a measure of the virus killing ability of the treatment. Detection of the amount of virus may also be done using classic analytical testing techniques such as ELISA or microscopic determination. The duration of the contacting with the reactive gas may be increased in order to further reduce the amount of active virus. The contacting of a surface with reactive gas may also be repeated to further reduce the activity of virus.

The virus may be a DNA virus or an RNA virus. The DNA or RNA virus may be further classified as single stranded (ss), double stranded ds), linear and/or circular. The entire virus genome may occupy either one nucleic acid molecule (monopartite genome) or several nucleic acid segments (multipartite genome). The different types of genome necessitate different replication strategies.

The virus may be identified by the common virus name or the disease caused by the virus. The virus may also be identified by the organism from which the virus originated or in which the virus is endemic. It is understood that the common virus names identified herein may refer to various strains of viruses that have similar characteristics or are genetically related to the viruses associated with the common virus name.

The virus may be a DNA virus, such as a virus from the DNA virus family of Asfarviridae (such as African swine fever virus (ASF)); Adenoviridae (such as Adenovirus and infectious canine hepatitis virus); Papovaviridae (such as Papillomavirus, polyomaviridae, and simian vacuolating virus); Parvoviridae (such as parvovirus B19 and canine parvovirus); Herpesviridae (such as herpes simplex virus, varicella-zoster virus (also known as chicken pox virus), cytomegalovirus, and Epstein-Barr virus); Poxviridae (such as smallpox virus, cow pox virus, sheep pox virus, orf virus, monkey pox virus, and vaccinia virus); Anelloviridae (such as Torque teno virus); or Pleolipoviridae (such as HHPV1, HRPV1, HGPV1, and His2V).

The virus may be an RNA virus, such as a virus from the RNA virus family of Reoviridae (such as reovirus and rotavirus (also called rotovirus)); Picornaviridae (such as enterovirus, rhinovirus, hepatovirus, cardiovirus, aphthovirus, poliovirus, parechovirus, erbovirus, kobuvirus, teschovirus, and coxsackie); Caliciviridae (such as norwalk virus); Togaviridae (such as rubella virus and alphavirus); Arenaviridae (such as lymphocytic choriomeningitis virus); Flaviviridae (such as dengue virus, hepatitis C virus, yellow fever virus, and Zika virus); Orthomyxoviridae (such as influenza virus, isavirus, and thogotovirus); Paramyxoviridae (such as measles virus, mumps virus, respiratory syncytial virus, Rinderpest virus, and canine distemper virus); Bunyaviridae (such as California encephalitis virus and hantavirus); Rhabdoviridae (such as rabies virus); Filoviridae (such as Ebola virus and Marburg virus); Coronaviridae (such as coronavirus); Astroviridae (such as astrovirus); Bomaviridae (such as Borna disease virus); Arteriviridae (such as arterivirus and equine arteritis virus); or Hepeviridae (such as hepatitis E virus).

Examples of rotavirus include A, B, C, D, E, F, G, H, I or J rotavirus. Examples of coronavirus include Middle East respiratory syndrome coronavirus (MERS), severe acute respiratory syndrome coronavirus (SARS), and COVID-19 virus, as well as coronaviruses that cause the common cold. The virus that causes COVID-19 is also known as severe acute respiratory syndrome coronavirus 2 (SARS-CoV-2). An example of arterivirus is porcine reproductive and respiratory syndrome virus (PRRSV).

Examples of influenza virus include influenza virus A, influenza virus B, and influenza virus C. Influenza virus variants are sometimes named according to the species (host) in which the strain is endemic or to which it is adapted. For example, the influenza virus may be known as bird flu (also known as avian flu), swine flu, human flu, equine flu, and canine flu. Influenza virus A species may be further classified by a combination of two groups of proteins: hemagglutinin or "H" proteins and neuraminidase or "N" proteins ("Influenza Type A Viruses". Centers for Disease Control and Prevention. https://www.cdc.gov/flu/avianflu/influenza-a-virus-subtypes.htm. Last reviewed Apr. 19, 2017, visited on Mar. 12, 2020). Examples of different serotypes of Influenza virus A include H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, H10N7.

The virus may be a reverse transcribing virus from the virus family of Retroviridae (such as human immunodeficiency virus (HIV)); Caulimoviridae (such as Caulimovirus, and Cacao swollen-shoot virus); or Hepadnaviridae (such as Hepatitis B virus).

The virus may be present on a product or a surface, or may be present in the air. The reactive gas may disarm virus that is present in the air in aerosol droplets or larger droplets. The reactive gas may contact the interior surfaces of a man-made structure. The man-made structure may be a vehicle, such as a plane, a train, or an automobile. The man-made structure may be a room or passage. The room may be a room in a hospital or a cruise ship cabin. The room may be a room or rooms in a hotel. The room may be an office or meeting space. The room may be a theater or sports arena.

FIGS. 1A, 1B, 1C, 1D, 1E and 1F are schematic illustrations of a variety of DBD systems which may be used to produce HVCP which produces a reactive gas. A DBD system includes a high voltage source, 10, having a ground which generates an alternating current, a first electrode, 20, a second electrode, 30, and an intervening dielectric, 40. One or more additional intervening dielectrics, 60, may also be present between the first and second electrode. In some configurations the dielectric may surround the first and/or second electrode. In some configurations, the charge accumulation on the electrodes, used in conjunction with the voltage waveform, may be used to estimate the power consumption of the DBD system, and may be measured by determining the voltage developed across a conventional capacitor or other sensor, 70. Preferably, a plenum, 50, is present, which defines a space between the electrodes where the HVCP and the reactive gas are produced, as shown in FIGS. 1A, 1B, 1C and 1F. However, the HVCP and reactive gas may also be produced in the vicinity of the dielectrics even when a clear plenum is not present in the DBD system, such as illustrated in FIGS. 1D and 1E. In some configurations, multiple electrodes, such as 3 to 21 electrode, 11 to 15, 4 to 8 electrodes, or 5 to 7 electrodes, with one or more intervening dielectrics between each pair of adjacent electrode, and optionally forming multiple plenums, may be used, such as that illustrated in FIG. 1F (where a frame, 80, may be used to hold each electrode-dielectric assembly (such as 40, 20, and 40) to define each plenum (50)); such an arrangement allows for the production of a greater amount of HVCP and therefore production of reactive gas, while maintaining the appropriate distance between electrodes and keeping the system compact. The configuration of the DBD system results in limiting of the current of any filamentary discharge that is formed between the electrodes so as to prevent the formation of a high current arc. In a preferred arrangement, a first electrode is fully enclosed in a dielectric, and a second electrode is grounded.

The electrodes may be formed from any conductive material, such as a metal. The dielectrics may be formed from any insulating material (dielectric material), such as ceramics, glass, organic materials, or plastics, including multiple layers of various compositions. The thickness of the dielectric, or different layers of dielectric, should be selected to limit the current of any filamentary discharge that may form between the electrodes. Selection of materials for the dielectric layers may have an effect on the reactive gas composition.

The distance between adjacent electrodes when the electrodes are parallel, or the shortest distance between adjacent electrodes when the electrode are not parallel, is preferably at most 30 cm (or 12 inches), and preferably is at least 0.5 cm (or 0.25 inches), such as 1 to 10 cm, or 2.5 to 6 cm (or 1 to 2 inches), including 2, 3, 4, 5, 6, 7, 8 and 9 cm. The high voltage source produces a voltage of at most 500 kV, more preferably 20 kV to 150 kV, including 30, 40, 50, 60, 70, 80, 90, 95, 100, 110, 120, 130 and 140 kV; having a frequency of at most 5000 Hz, more preferably 10 to 100 Hz, such as 50 to 60 Hz. Time variant (that is, pulsed) DC power may also be used. Although the frequency is chosen primarily for convenience (for example, 50 or 60 Hz AC power is available from the municipal power grid), voltage is selected to ensure the production of HVCP.

The structure of the electrode system and/or dielectric barrier discharge system may be the system described in U.S. patent application Ser. No. 16/442,380.

Different selection of working gases and working gas mixtures will affect the species present in the reactive gas produced by the HVCP. Examples of gases which may be used to prepare the HVCP include oxygen ($O_2$); nitrogen (N2); water vapor ($H_2O$); inert and noble gases such as helium (He), neon (Ne), argon (Ar), krypton (Kr), xenon (Xe) and sulfur hexafluoride ($SF_6$); hydrogen ($H_2$); carbon dioxide ($CO_2$) and carbon monoxide (CO); halogens and pseudo-halogens such as fluorine ($F_2$), chlorine ($Cl_2$), bromine ($Br_2$), and cyanogen ($(CN)_2$); acidic gases such as hydrogen sulfide ($H_2S$), hydrogen fluoride (HF), hydrogen chloride (HCl), and carbonyl sulfide (COS); ammonia ($NH_3$); hydrazine ($H_4N_2$); nitrogen trifluoride ($NF_3$); chlorine dioxide ($ClO_2$); hydrocarbons such as methane ($CH_4$), ethane ($C_2H_6$) and acetylene ($H_2C_2$); alcohols such as methanol ($CH_3OH$) and ethanol ($C_2H_5OH$); and mixtures thereof. Preferred gases include air and MA65 (a mixture of 65% $O_2$, 30% $CO_2$, and 5% $N_2$). Increasing the amount of water vapor in the gas may be used to reduce ozone present in the reactive gas. Increasing the amount of noble gas, such as helium, may be used to reduce the voltage needed to produce the HVCP. The pressure of the gas use to prepare the HVCP is conveniently selected as ambient or atmospheric pressure, but other pressures may be used, such as 10 to 50000 Torr, more preferably 100 to 1000 Torr, such as 760 Torr (atmospheric pressure).

The reactive gas contains a variety of reactive and excited species, and the reactive gas always contains at least one (and typically more than one) reactive and/or excited species which is not present in the working gas. When the working gas contains oxygen (for example, $O_2$, $CO_2$, and/or $H_2O$) ozone may form; however, the properties and reactions of the reactive gas are not explained by the presence of ozone alone, and the reactive gas always contains other reactive and excited species in addition to any ozone (which may, or may not, be present in the reactive gas). In addition to ozone, other reactive and excited species which may be present in reactive gas include: singlet oxygen ($^1O_2$) and other excited molecular species (both vibrationally excited molecules and electronically excited atoms and/or molecules, such as $O_2$, $H_2$, $N_2$, CO, $CO_2$, $H_2O$, He, Ne, Ar, Kr and Xe), hydroxyl radical (HO·), nitrogen oxides (such as $N_2O$, NO, $NO_2$, $NO_3$, $N_2O_3$, $N_2O_4$ and $N_2O_5$), hydrogen peroxide ($H_2O_2$), hydroperoxyl ($HO_2$), $HNO_x$ species (such as $HNO_4$, $HNO_3$ and HNO), atomic radicals (such a O, F, Cl, N and H), and molecular radicals (such as hydrocarbon radicals, which may also contain one or more of oxygen, nitrogen, fluorine and chlorine). Preferably, the reactive gas has at least one additional reactive and/or excited species in addition to ozone and $NO_2$ (or $N_2O_4$) (which may, or may not, be present). Unlike HVCP, reactive gas is not a plasma and does not contain free electrons. Preferably, the reactive gas contains at least 2 different reactive and/or excited species listed above, more preferably at least 3 different reactive and/or excited species listed above, even more preferably at least 4 different reactive and/or excited species listed above, and most preferably at least 5 different reactive and/or excited species listed above, including 2-10 or 3-8 or 4-6 different reactive and/or excited species listed above.

It is also possible to capture and store the reactive gas in a container for later use. Preferably, the stored reactive gas is used to treat a product or surface within 24 hours after it is produced, more preferably within 12 hours, most preferably within 6, even more preferably within 3 hours.

The reactive gas may also be captured and stored by cooling to extremely low temperatures, for example using liquid nitrogen as a coolant, or using liquid helium as a coolant. When captured and stored at such low temperatures, the reactive gas may be stored for extended periods of time, for example 1 day to 6 weeks, and possibly longer. Containers, such a glass or metal containers used to store other liquefied or solidified gases, may be used.

A reactive gas treatment system includes either a DBD system or stored reactive gas, and a treatment chamber. The reactive gas treatment system also includes a device, mechanism, or a configuration for moving the reactive gas away from the DBD system (which produces a HVCP, which in turn produces the reactive gas) or from a container having stored reactive gas, and into or throughout the treatment chamber; this may be a fluid connection between the DBD system and the treatment chamber. Preferably, the treatment chamber is not sealed; such an unsealed chamber would include a treatment chamber with a gas outlet. Preferably, the treatment chamber has a volume of at least 28 liters (or 1 cubic foot), more preferably a volume of at least 1 cubic meter, and even more preferably at least 8 cubic meters. Examples of treatment chambers include rooms, bins, grain dryers, silos, tanks and shipping containers.

The reactive gas system may be used to carry out a method of treating a product and/or a surface, by supplying the reactive gas (either from stored reactive gas, or by generating a HVCP using a DBD system), and distributing the reactive gas into or throughout the treatment chamber. Examples of a device, mechanism, or configuration for moving the reactive gas includes convection, a gas pathway or gas line, a fan, and supplying flowing or pressurized working gas to the DBD system. Preferably, the product or surface treated by the reactive gas is not heated (that is, its temperature is not increased) by the method of treatment by more than 40° C., more preferably by not more than 20° C., even more preferably by not more than 10° C., and most preferably by not more than 5° C., such as no heating of the product or surface. Treatment with the reactive gas is a non-thermal processing method. Preferably, products or surfaces are not exposed to radiation (such as UV light) produced by a HVCP during the method. Optionally, air, a working gas, or another gas (such as a noble gas or nitrogen) may be used to flush the reactive gas out of the treatment chamber, or the treatment chamber may be evacuated. The method may be optionally repeated 1, 2, 3 or more times, to provide multiple treatments to products or surfaces. Optionally, product may be sealed into a container and/or refrigerated after treatment with a reactive gas. Preferably, the product to be treated is not enclosed in a sealed or substantially sealed contain, such as a container have a volume of at most 10 gallons, or at most 6 gallons, during treatment. Preferably, the HVCP is not produced inside a sealed container, such as a container have a volume of at most 10 gallons, or at most 6 gallons.

The reactive gas produced by the HVCP is transported away from the site of production of the HVCP (to avoid direct exposure of the product or surface to the HVCP), by diffusion or gas transfer. Preferably, the distance between the plasma and the product or surface to be treated is at least a distance of 5 cm, such as at least 10 cm, at least 50 cm, and at least 1 meter (or 3.28 feet), more preferably at least 3 meters, for example 3 to 300 meters, including 5, 10, 20, 30, 40 and 50 meters. In most configurations, the reactive gas is allowed to flow while it is in contact with a product or surface to be treated, although it is also possible to produce the reactive gas and transfer it to a site to treat the product or surface, and confine the gas to the treatment location for a period of time. Examples of flow rates for transferring the reactive gas to a location for contact with a product or surface include 10 to 3000 meters/minute, 30 to 2500 meters per minute, and 1000 to 2000 meters/minute, such as 50, 100, 200, 300, 400, 500, 750, and 1500 meters/minute. The reactive gas is allowed to contact the product or surface for at least 1 second, for example at least 2 seconds, at least 10 seconds, at least 30 seconds, at least 1 minute, at least 10 minutes, at least 30 minutes, at least 35 minutes, at least 1 hour, at least 6 hours, or at least 12 hours. Examples of contact times include 1 second to 12 hours, 10 seconds to 1 hour, 1 minute to 35 minutes, including 5 seconds, 15 seconds, 2 minutes, 5 minutes, 20 minutes, 35 minutes, 40 minutes, 2 hours, 3 hours, 4 hours and 5 hours.

Figure 2:
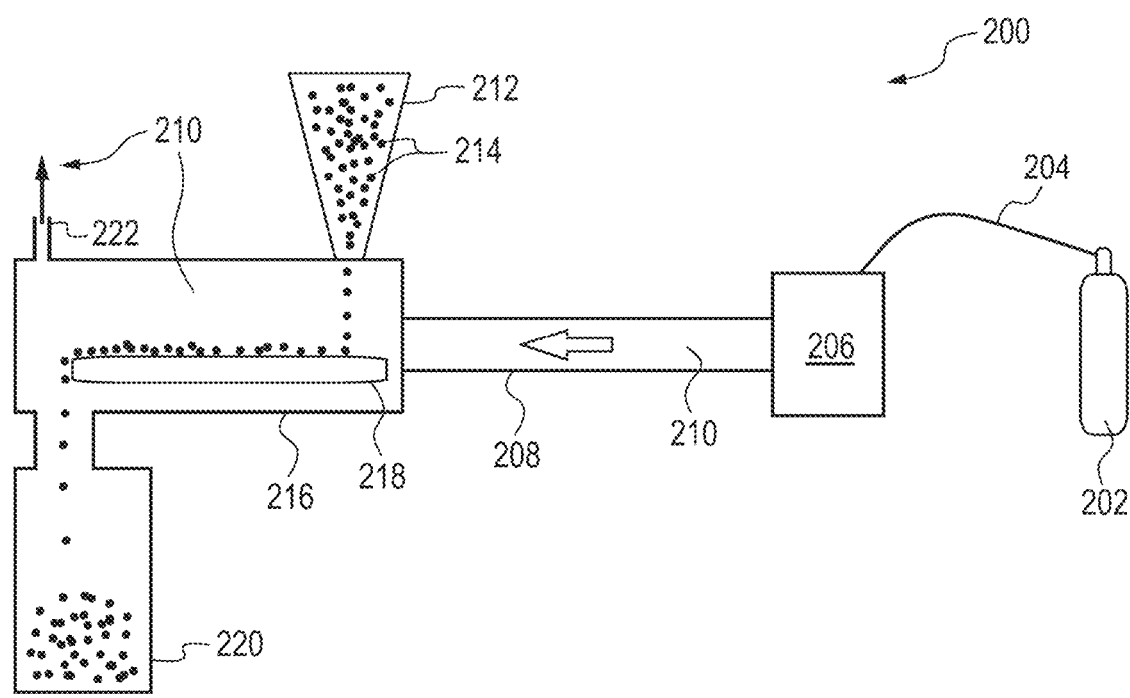
FIG. 2 is a schematic illustration of a reactive gas treatment system for continuous treatment of a product or a surface with a reactive gas.

FIG. 2 is a schematic illustration of a reactive gas treatment system, 200, for continuous treatment of a product or a surface with a reactive gas. The system includes a DBD system, 206, for generating a HVCP to produce a reactive gas, 210. The reactive gas flows along a gas pathway, 208, into a treatment chamber, 216, and then out a gas outlet, 222. Product, 214, to be treated or which has a surface to be treated, may be stored in a hopper, 212, as it is fed into the treatment chamber, and onto a conveyor, 218, which moves the product through the treatment chamber and into a receiving bin, 220, for hold the product after it has been contacted with the reactive gas. Also illustrated is a gas source, 202, such as a gas tank, which provides a working gas from which the HVCP is formed, and a gas line, 204, which supplied the DBD system with the working gas. The reactive gas may be diluted with additional working gas as it flows through the system. The transport of the reactive gas from the DBD system to the treatment chamber is by way of a pressure differential between the DBD system (at higher pressure from introduction of the working gas) and the treatment chamber (at lower pressure due to the gas outlet). Optionally, the gas outlet may be connected back to the DBD system by a second gas line, allowing for recycling of the working gas and any remaining reactive gas. Optionally, the DBD system may be located inside the treatment chamber, avoiding the need for a gas pathway. In a variation, the working gas may be air, and the transport of the reactive gas may be caused by a fan located in the gas pathway (blowing the reactive gas into the treatment chamber) or at the back of the DBD system (blowing air through the DBD system). Optionally, the conveyor may transport the product on a screen to ensure that the reactive gas comes into contact on all surfaces of the product. Furthermore, product may be moved through the treatment chamber on a plurality of conveyors, where the product is shifted around as it moves from a first conveyor to a second conveyor, ensuring that the reactive gas comes into contact with all surfaces of the product. In another variation, the DBD system may be eliminated, by using a stored reactive gas as the gas source and transporting the reactive gas directly to the treatment chamber. A variety of different conveyors may be used, such as a permeable belt conveyor, a screw, a tunnel dryer, a grain dryer, a fluid bed dryer or a cylindrical dryer.

Figure 3:
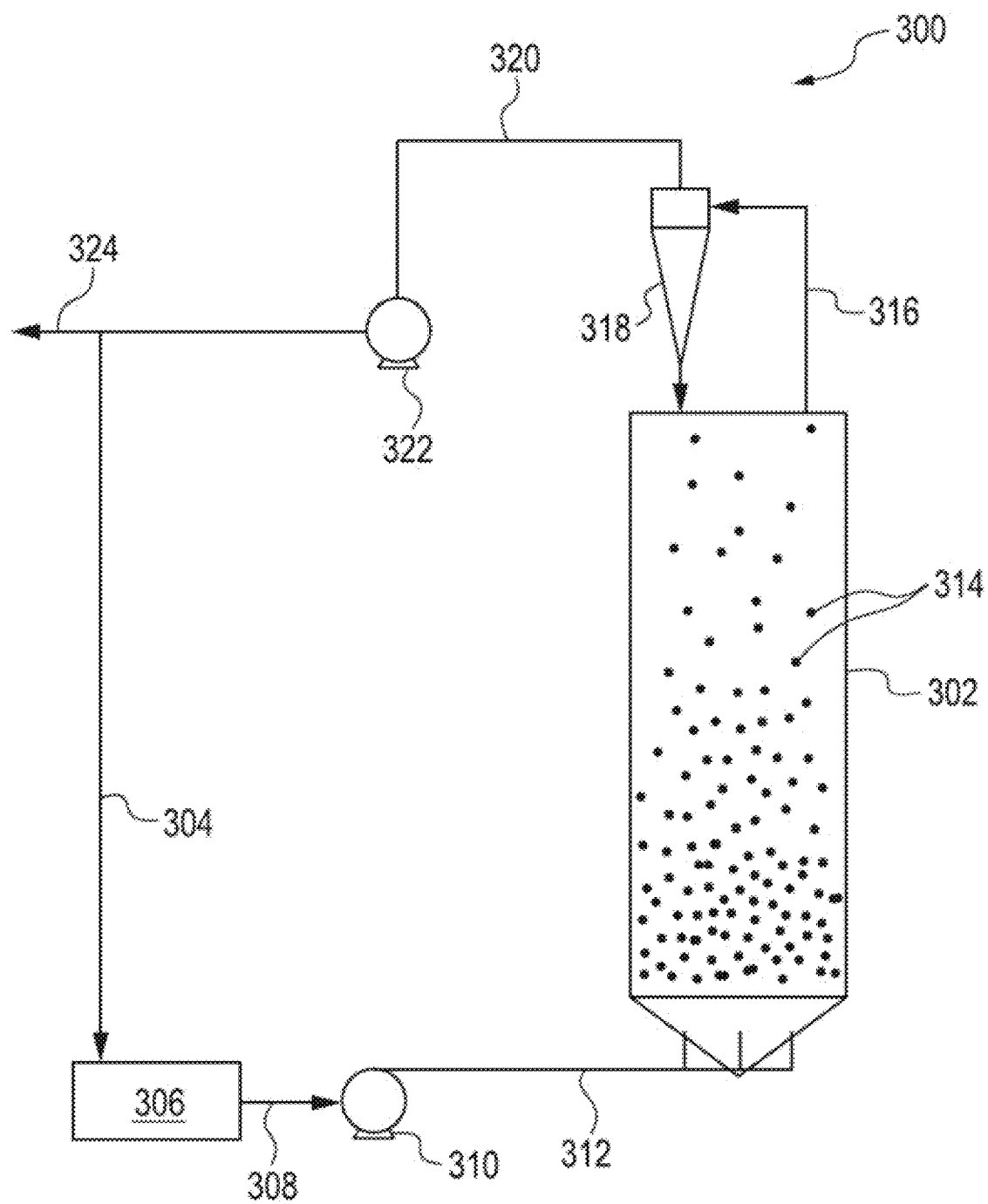
FIG. 3 is a schematic illustration of a reactive gas treatment system for batch treatment of a product or a surface with a reactive gas.

FIG. 3 is a schematic illustration of a reactive gas treatment system, 300, for batch treatment of a product or a surface with a reactive gas. The system includes a DBD system, 306, for generating a HVCP to produce a reactive gas. The reactive gas flows along gas pathways, 308 and 312, into a treatment chamber, 302, and then out through a gas pathway, 316, through an optional product recovery trap, 318, along a gas pathway, 320, and out through a gas outlet, 324. Some or all of the reactive gas and working gas may be recycled back to the DBD system through an optional gas pathway, 304. The reactive gas and working gas is propelled through the system by fans, 310 and 322. Product, 314, to be treated or which has a surface to be treated, is present in the treatment chamber; as illustrated the reactive gas is fed in through the bottom of the treatment chamber to create a fluidized bed from of the reactive gas and the product to ensure treatment of all surfaces of the product. The product recovery trap may be used to capture any product which exits the treatment chamber and into the gas pathway and return it back to the treatment chamber. The treatment chamber may be a silo in the system illustrated; other treatment chambers include a fluid bed, a mechanical fluid bed, and a bin. The reactive gas may be diluted with addition working gas as it flows through the system. As illustrated, the working gas may be air, but optionally the gas pathway, 304, may be connected to a gas source for supplying a working gas to the DBD system. In another variation, the DBD system may be eliminated and replaced with stored reactive gas.

Examples of products includes fresh foods (such as fruits, vegetables, grains, beans, seeds, meat, dairy products, eggs, and spices or seasonings), seafood (fish and shell fish, and their parts), prepared foods, frozen foods, processed foods prior to packaging (water, beverages, baby food, liquid eggs, fruit juice, flour, oil, nutritional product, vitamins, nutraceuticals and baked foods), packaged products (for treatment of the exterior of the packages), animal feed, cans, bottles, plastic containers, food containers, cookware and utensils; pills, capsules, unit dosage forms and powders; medical devices and medical equipment, both before use and after use; laboratory glass and plastic ware; ceramic products; metal products; and leather and wood products.

If disinfection is not accomplished by treatment with the reactive gas, successive treatments may be conducted. For example, 1 to 10 treatments may be carried out, or 2 to 9 treatments, including 3, 4, 5, 6, 7 or 8 treatments may be carried out. Similarly, the time of treatment may also be extended.

Figure 4:
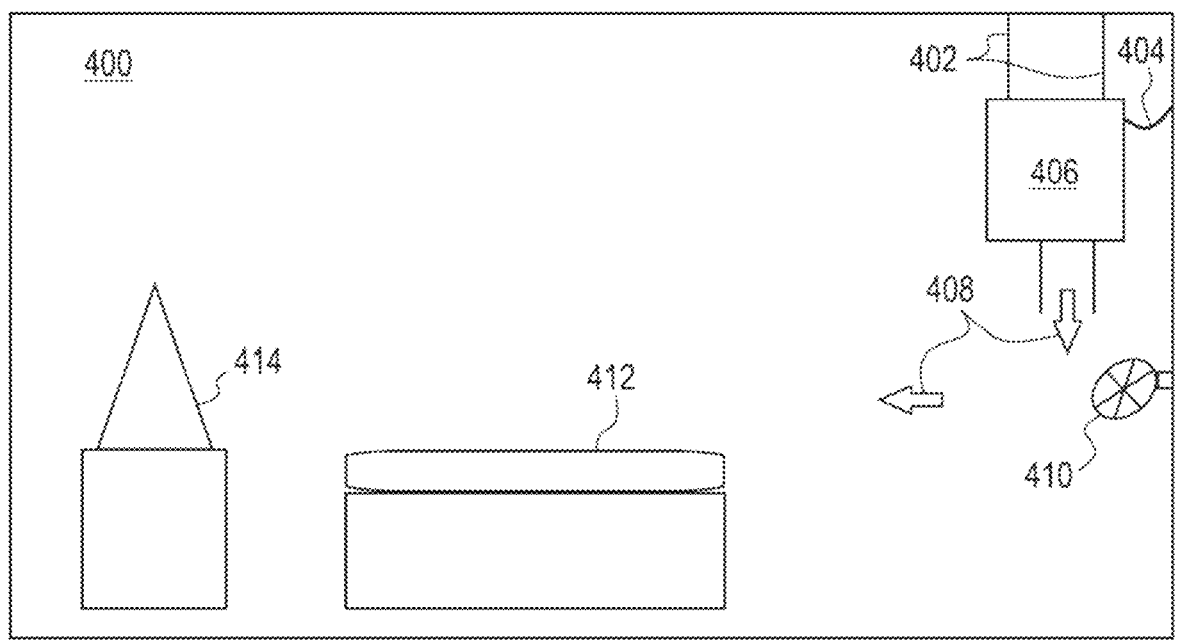
FIG. 4 is a schematic illustration of a reactive gas treatment system for treatment of equipment and/or surfaces with an enclosed space.

FIG. 4 is a schematic illustration of a reactive gas treatment system for treatment of equipment and/or surfaces with an enclosed space, such as a room, a shipping container, a trailer or a refrigerated truck. Within the treatment chamber, 400, which here is the enclosed space, is a DBD system, 406, for generating a HVCP to produce a reactive gas, 408. A fan, 410, is used to distribute the reactive gas throughout the enclosed space. Also illustrated are product or surfaces to be treated, which includes the walls or interior surfaces of the enclosed space, optional equipment, 414, such a medical equipment (for example, surgical instruments, masks, assisted breathing equipment, and vital sign monitors), and/or optional surfaces, 412, such as a surgical table, to be treated with the reactive gas. Optionally, supports, 402, could be used to mount the DBD system to the top or the sides of the enclosed space, or the DBD system could be place on the floor of the enclosed space. Optionally, a working gas supply could be supplied by a gas line, 404, connected to a gas supply (not illustrated). Alternatively, the enclosed space could be filled with a working gas. In another configuration, the DBD system could be replaced with stored reactive gas.

EXAMPLES

The following examples are test systems to show the effects and properties of reactive gas, where a HVCP was used to produce the reactive gas. In a typical system, the scale would be increased to achieve treatment of commercially significant amounts of product. All HVCP was produced using power at 60 Hz.

Example 1: The Effect of Reactive Gas on Viral Activities and Inactivation: Use of MS2 Bacteriophage Model for Screening Reactive Gas Effectiveness as an Antiviral Agent This example describes the use of a reactive gas transported 21 feet (640 cm) on a MS2 bacteriophage for effectiveness on killing viruses. The MS2 bacteriophage is an RNA virus that infects Escherichia coli (E. coli) and other bacterial members of Enterobacteriaceae. Since most human viral pathogens are RNA viruses, MS2 bacteriophage (a non-human pathogen) was chosen as a model system for viral inactivation. MS2 bacteriophages are a commonly used model for human viruses (Kuzmanovic, D. A., et al., "Bacteriophage MS2: Molecular Weight and Spatial Distribution of the Protein and RNA Components by Small-Angle Neutron Scattering and Virus Counting", Structure, Vol. 11, 1339-1348 (2003)).

Growing Host Bacterial Culture:

The MS2 bacteriophage host bacterium, used in this study was Escherichia coil (E. coli, strain K-12, ATCC 15597). The E. coli (ATCC 15597) in its original vial was purchased from American Type Culture Collection (ATCC) (Manassas, Va.) and reconstituted by adding 1 ml of fresh broth medium (1% Tryptone, 0.1% Yeast Extract, and 0.8% NaCl in deionized water). The reconstituted culture (100 μl), was withdrawn from the vial and used to inoculate 30 ml of same broth medium in culture flasks and grown in a thermal incubator overnight at 37° C. The resulting E. coli culture was then used for propagation of MS2 bacteriophage and screening assay.

MS2 Bacteriophage Propagation

The Bacteriophage, MS2 (ATCC 15597-B1) was propagated in its bacterial host cells, E. coli (strain K-12, ATCC 15597) according to ATCC procedure without using soft/top-agar overlay. The host bacterial culture cells were grown overnight in broth at 37° C., as described above. Subsequently, 1.0 ml of host bacterial cells suspension was added to the surface of agar plates and gently tilted to ensure the entire surface coverage with host bacterial cells. The excess liquid was then aspirated from the agar plate and plates were allowed to dry. Solutions of various dilutions of MS2 phage suspension in broth was spotted on the surface of agar plate and incubated overnight at 37° C. After overnight growth, 5 ml of SM buffer was added to each agar plate and stored at 4° C. for 3 hours with periodic gentle shaking. The SM buffer suspensions were collected and transferred into 50 ml polypropylene tubes and fresh SM buffer (5 ml per plate) was added into each plate followed by further incubation at 4° C. for 15 minutes with periodic suspension. The buffer was collected and pooled together with previous buffer in the 50 ml tubes and plates discarded. The pooled SM buffer-MS2 phage suspension was centrifuged at 5000×g for 15 minutes at 4° C., to sediment the cellular debris and agar pieces, and the supernatants were collected. The resulting supernatants were passed through a 0.22 μM Millipore filter to remove the host bacteria cells, and the filtrate containing the recovered MS2 phage was stored at 4° C. for experimental use.

Reactive Gas Deactivation of MS2 Phage

For deactivating MS2 virus with reactive gas, 1 ml of filtered MS2 phage supernatant was spotted on a circular Whatman filter paper (diameter 90 mm) purchased from General Electric Company (GE Healthcare Life Sciences, Pittsburgh, Pa.). The filter papers were then dried through evaporation and then exposed to reactive gas transported 21 feet (640 cm) for 30-90 minutes produced using a DBD system at a voltage of 76 kV. The electrode gap of the device producing the plasma was 1.5 inches. After reactive gas treatment, the papers were sliced into 15 ml sterile tubes and MS2 virus recovered from sliced filter paper pieces through extraction with 5 ml per tube of SM buffer. The viral activity in the paper extracts was determined by high-throughput screening using clear 96-well flat bottom plates (purchased from Midwest Scientific (MidSci), St. Louis, Mo.) and the host bacterial culture (E. coli). Briefly, E. coli culture grown overnight, was diluted to a cell density of 1000 cells/ml suspension in nutrient broth; and aliquoted into 96-well plate (275 μl/well). This was immediately followed by addition of 25 μl of MS2 phage paper extract. The inoculated 96-well plate was then incubated overnight at 37° C. and E. coli growth kinetics monitored overnight for 24 hours. At the end of 24 hours, an optical density (OD) reading at 660 nm was taken and used for computing bacterial growth reversal by reactive gas deactivated MS2 virus. The negative (medium broth alone) and positive (bacterial culture alone) controls were also run in the same plate and in turn used for computing bacterial growth inhibition by the MS2 phage. Both reactive gas untreated and treated MS2 phage were compared with positive control wells and percentage growth of E. coli calculated for all plasma treated virus.

The bacterial growth percentage inhibition by MS2 phage recovered from the control filter paper extracts (reactive gas untreated) and reactive gas exposed MS2 phage paper extracts were determined by comparing their respective bacterial growth with that of the positive control wells (wells without MS2 phage exposure). The results for this study are depicted below.

Figure 5:
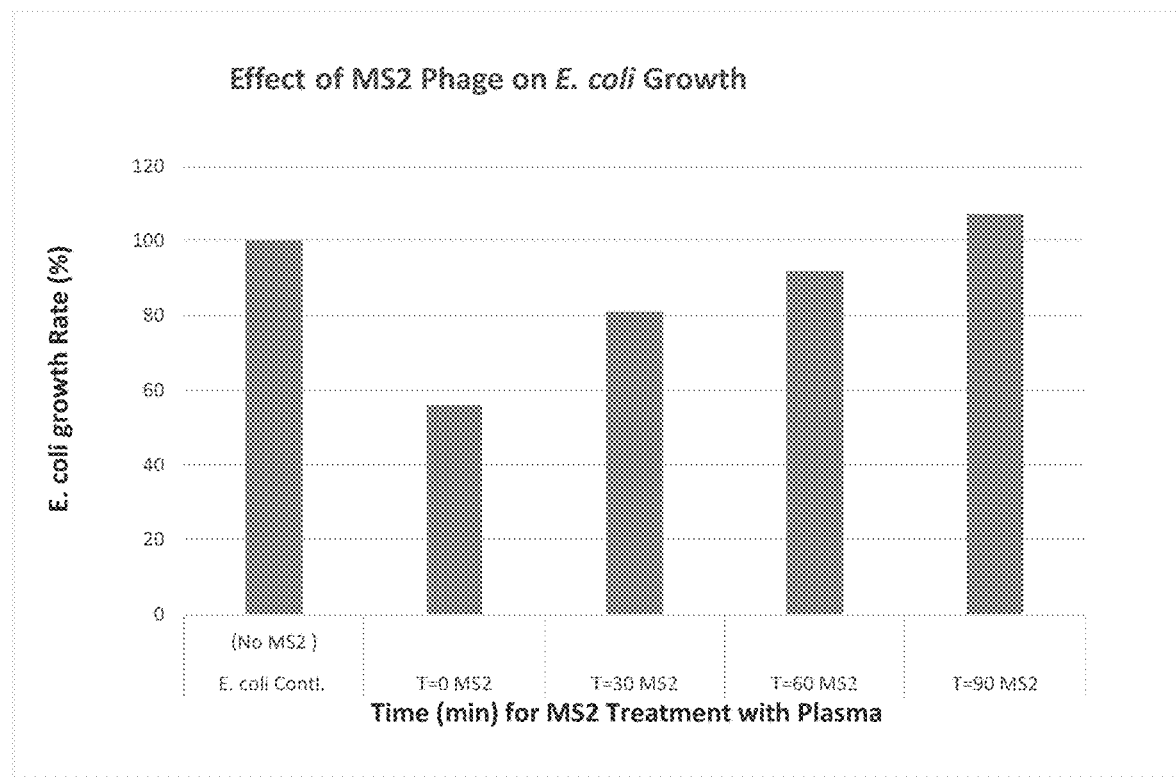
FIG. 5 is a graph showing effect of MS2 phage on *E. coli* growth rate for various data sets, relative to the *E. coli* control.
Figure 6:
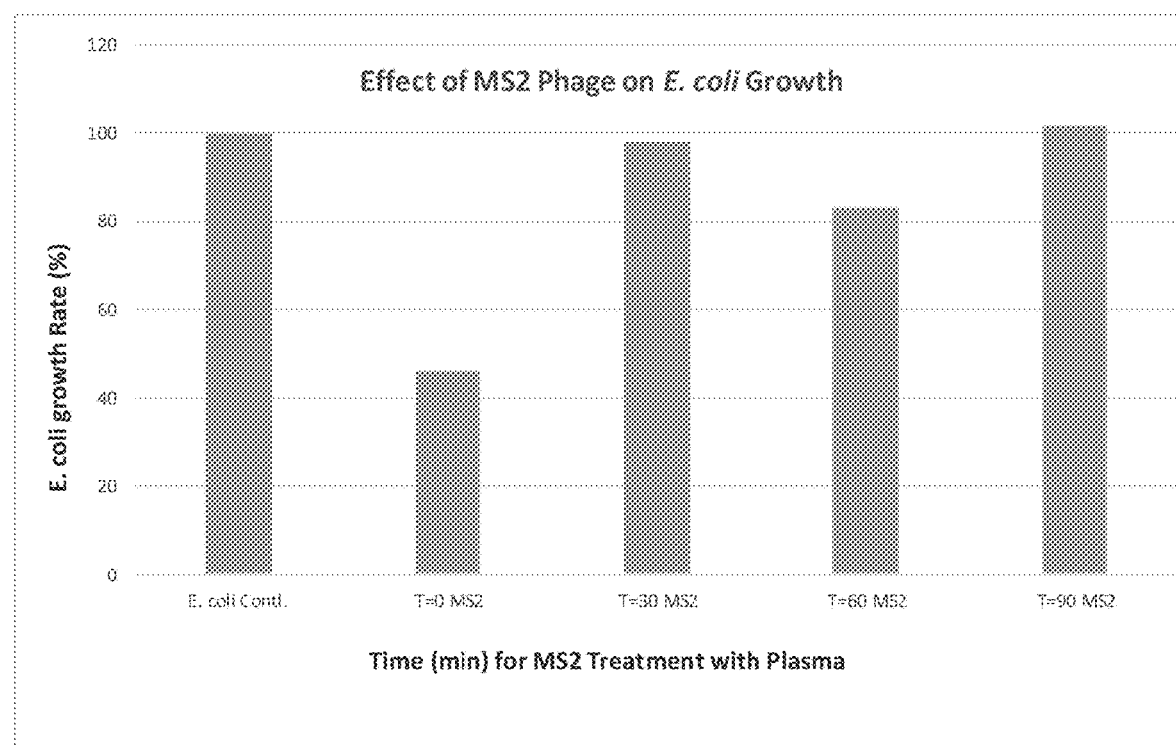
FIG. 6 is a graph showing effect of MS2 phage on *E. coli* growth rate for various data sets, relative to the *E. coli* control.
Figure 7:
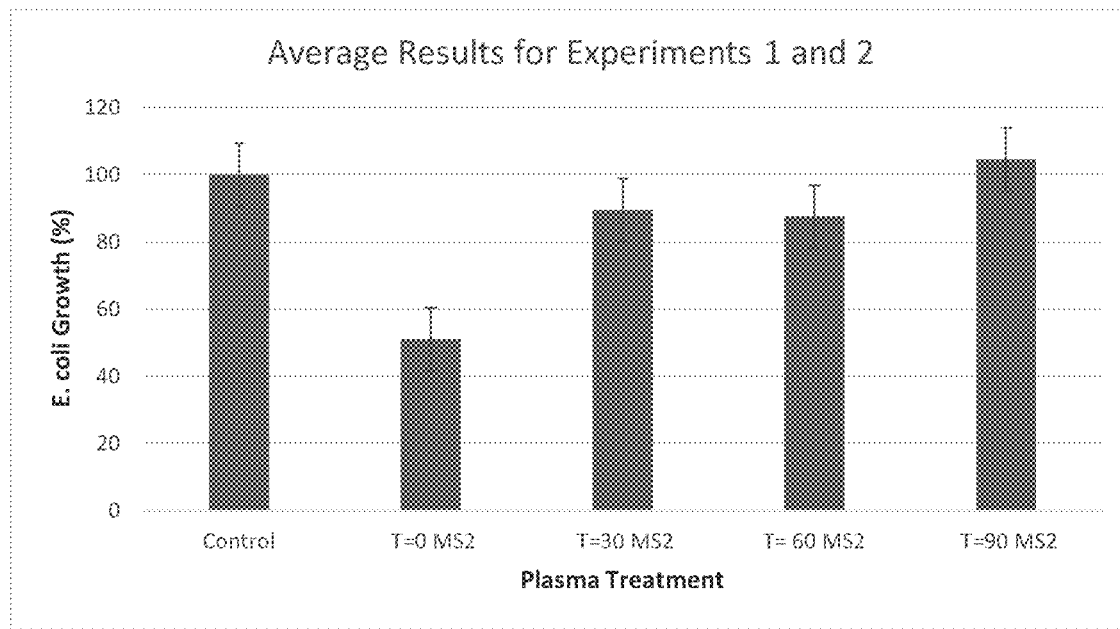
FIG. 7 is a graph showing effect of MS2 phage on *E. coli* growth rate for various data sets, relative to the *E. coli* control.

Results:

The tabulated data presented here are from two independent experiments performed on different dates. As demonstrated by these results, exposure of MS2 phage to reactive gas significantly deactivated the virus and reversed its lytic activities towards its bacterium host, E. coli in all exposure time studied. As shown in the graphs of FIGS. 5, 6 and 7, untreated MS2 phage reduced bacterial growth by 50 percent. Exposure of virus to reactive gas for 30, 60 and 90 minutes respectively reversed this growth inhibition in a linear fashion proportional to duration of exposure of virus to reactive gas. This suggests that the MS2 phage was significantly reduced or deactivated by reactive gas thus allowing its host bacterium E. coli to grow normally (without being lysed by the virus). In Experiment 1(a), the data was obtained at a 24-hour end point.

| 1(a). Experiment 1 | | | | | |
|---|---|---|---|---|---|
| Treatment | E. coli Control | T = 0 MS2 | T = 30 MS2 | T = 60 MS2 | T = 90 MS2 |
| | 0.691 | 0.463 | 0.44 | 0.734 | 0.765 |
| | 0.708 | 0.338 | 0.326 | 0.735 | 0.775 |
| | 0.717 | 0.383 | 0.755 | 0.728 | 0.778 |
| | 0.722 | 0.402 | 0.754 | 0.407 | 0.697 |
| Average OD 660 | 0.705 | 0.397 | 0.569 | 0.651 | 0.754 |
| E. coli Growth Rate (%) | 100 | 56 | 81 | 92 | 107 |

| Summary: | | | | | |
|---|---|---|---|---|---|
| MS2 Reactive Gas Treatments (Min) | E. coli Control (No MS2) | T = 0 MS2 | T = 30 MS2 | T = 60 MS2 | T = 90 MS2 |
| E. coli Growth (%) | 100 | 56 | 81 | 92 | 107 |

-continued

| 1(a). Experiment 1 | | | |
|---|---|---|---|

*E. coli* (host cell) count from MS2-negative, MS2-positive, and MS2-RGS treatments. Experiment 1 Results.

| Treatment | % Live Host Cell | % Host cell Mortality | % RGS Deactivation of MS2 phage (Normalized) |
|---|---|---|---|
| Negative Control | 100 | 0 | 0 |
| Positive control | 56 | 44* | 100** |
| RGS Treated T = 30 | 81 | 19* | 56.81** |
| RGS Treated T = 60 | 92 | 8* | 81.81** |
| RGS Treated T = 90 | 107 | −7* | 100** |

*normalized to negative control host cell count.
**normalized to positive host cell mortality.

| 2(a). Experiment 2 | | | | | |
|---|---|---|---|---|---|
| Reactive Gas Treatments | *E. coli* Control | T = 0 MS2 | T = 30 MS2 | T = 60 MS2 | T = 90 MS2 |
|  | 0.708 | 0.409 | 0.693 | 0.433 | 0.723 |
|  | 0.717 | 0.239 | 0.676 | 0.419 | 0.729 |
|  | 0.722 | 0.332 | 0.723 | 0.778 | 0.72 |
|  | 0.715 |  | 0.723 | 0.743 | 0.739 |
| Average OD660 | 0.716 | 0.327 | 0.704 | 0.593 | 0.728 |
| *E. coli* Growth Rate (%) | 100 | 46 | 98 | 83 | 102 |

| Summary: | | | | | |
|---|---|---|---|---|---|
| MS2 Reactive Gas Treatments (Min) | *E. coli* Control | T = 0 MS2 | T = 30 MS2 | T = 60 MS2 | T = 90 MS2 |
| *E. coli* Growth (%) | 100 | 46 | 98 | 83 | 102 |

*E. coli* (host cell) count from MS2-negative, MS2-positive, and MS2-RGS treatments. Experiment 2 Results.

| Treatment | % Live Host Cell | % Host cell Mortality | % RGS Deactivation of MS2 phage (Normalized) |
|---|---|---|---|
| Negative Control | 100 | 0 | 0 |
| Positive control | 46 | 54* | 100** |
| RGS Treated T = 30 | 98 | 2* | 96.30** |
| RGS Treated T = 60 | 83 | 17* | 68.52** |
| RGS Treated T = 90 | 102 | −2* | 100** |

*normalized to negative control host cell count.
**normalized to positive host cell mortality.

Media and Reagents for Host Bacterium and MS2 Phage of Example 1
*Escherichia* Medium Preparation:

| (I) Agar Plate | | |
|---|---|---|
| Ingredients | 1 liter | 500 mL |
| 1. Tryptone | 10.0 g | 5.0 g |
| 2. Yeast Extract | 1.0 g | 0.5 g |
| 3. NaCl | 8.0 g | 4.0 g |
| 4. Agar | 15.0 g | 7.5 g |

950 ml of deionized water was added for 1 liter or 475 ml for 500 ml media volumes. Medium was autoclaved at 121° C. and aseptically, solution B added to the media after autoclaving and cooling down (that is, 50 ml for 1 liter volume or 25 ml for 500 ml volume). The medium was poured into 100 mm Petri Plates prior solidifying (10 ml per plate). The Agar Plates were store at 4° C. and used as needed.

(II) Solution B: 50 ml or 500 ml
The Solution B was prepared according to ATCC recommendation:

| 50 ml | | 500 ml | |
|---|---|---|---|
| 1. | Glucose - 1.0 g | 1. | Glucose - 10.0 g |
| 2. | $CaCl_2$ - 0.294 g | 2. | $CaCl_2$ - 2.94 g |
| 3. | Thiamine - 10.0 mg | 3. | Thiamine - 100.0 mg |

The resulting solution was sterilized by filtering through 0.22 μM filter.

| (III) Nutrient Broth | | |
|---|---|---|
| Ingredients | 1 liter | 500 ml |
| Tryptone | 10.0 g | 5.0 g |
| Yeast Extract | 1.0 g | 0.5 g |
| NaCl | 8.0 g | 4.0 g |

After weighing broth ingredients, as in agar plate medium; 950 ml or 475 ml deionized water was added for 1 liter or 500 ml media. The broth was autoclaved at 121° C. and aseptically solution B added, after autoclaving and cooling down (50 ml for 1 liter volume or 25 ml for 500 ml broth). The broth medium was aliquoted into sterile glass flasks and store at room temperature for future use.

| (IV) Top Agar Nutrient | | |
|---|---|---|
| Ingredients | 1 liter | 500 ml |
| Tryptone | 10.0 g | 5.0 g |
| Yeast Extract | 1.0 g | 0.5 g |
| NaCl | 8.0 g | 4.0 g |
| Agar | 5.0 g | 2.5 g |

The soft/top agar was prepared in same way as plate agar medium. Half of the Agar amount was weighed into top agar medium (usually agar plates medium contains 15 g agar (1.5% w/v) and top agar 5-7.5 g agar (0.5-0.75% w/v). After autoclaving, cooling and adding solution B, the soft medium was aliquoted into sterile glass tubes (4 ml per tube) and store at room temperature for future use as needed.

(V) MS2 Phage Suspension Buffer (SM Buffer): SM Buffer (1 liter)

5.8 g NaCl (100 mM)
2 g MgSO4 · 7 H2O (8 mM)
50 ml 1M Tris-Cl (pH 7.5) (50 mM)
5 ml 2% gelatin

Example 2: Evaluation of the Effectiveness of Reactive Gas (RGS) as an Antiviral Agent Using Zika Virus (ZIKV)

This example describes the use of a reactive gas transported 21 feet (640 cm) on a Zika virus for effectiveness on killing viruses. In this study, effort was made to determine the effectiveness of RGS in deactivating Zika virus infectivity. This virus is one of the emerging global pathogens responsible for causing birth defects like microcephaly. Like most of new classes of viruses, Zika virus has no approved therapies or vaccines and any antiviral agent with inhibitory effects towards its activities will be a useful tool to prevent its infection. In this preliminary study, we tested whether RGS is suitable as an antiviral agent for the deactivation Zika virus.

Materials and Methods

Host Cells, Zika Virus, and Regents

Vero cells (ATCC CCL-81), used for Zika virus propagation and infection were purchased from American Type Culture Collection (ATCC, Manassas, Va.). Zika virus (ATCC VR-1843 PQ, strain PRVABC59) was also bought from ATCC. The cells were grown in high glucose Dulbecco's modified Eagles medium (DMEM, obtained from ATCC) and supplemented with 10% heat-inactivated fetal bovine serum (FBS), 4 mM L-glutamine, 100 µg/ml streptomycin, 100 units/ml penicillin, 1 mM sodium pyruvate and non-essential amino acids. Cells were cultured and maintained at 37° C. in 5% $CO_2$ humidified incubator. All tissue culture grade reagents and chemicals were either obtained from ATCC or Millipore-Sigma (St. Louis, Mo.) and Thermo Fisher Scientific (Waltham, Mass.).

Propagation of Zika Virus

The Zika virus (strain PR VABC59) used in this study was propagated by inoculating 70% confluent Vero cells in T75 tissue culture flasks for 2 hours in 3 ml DMEM medium without FBS, at a multiplicity of infection of 0.01 and 0.025, respectively. Then 20 ml of fresh DMEM medium with 10% FBS was added and cells incubated at 37° C. in a 5% $CO_2$ humidified chamber. The cytopathic effect (CPE), used as a measure of host cells killed by Zika virus was monitored by observation under light microscopy. The virus was harvested when Vero cells showed 70% or more cells death or detachment due to CPE. The spent medium was removed and centrifuged for 5 minutes at 3000 rpm. The resulting supernatant was passed through 0.22 µM Millipore filter to remove host cells residue and any contaminating bacteria. The Zika virus containing filtrate was aliquoted and stored at −20° C. for future experiments.

RGS Deactivation of Zika Virus

The RGS deactivation of Zika virus (ZIKV PRVABC 59) was performed according to established protocol (Muller et al, 2016). Briefly, Whatman disc filter papers (90 mm diameter) were inoculated with 600 µl of Zika virus spent medium and immediately exposed to RGS. Filter papers for the control experiment were only inoculated with host cell in Dulbecco's modified Eagles medium (DMEM) used for viral propagation (negative control). Two sets of inoculated filter papers were treated (test) with RGS for 45 and 90 minutes at 80 kV (Table 4), followed by virus extraction with sterile phosphate buffered saline (PBS, 1×). One set of inoculated filter paper that was not treated with RGS to serve as the positive control and it was immediately processed for virus extraction. The experiment was conducted in duplicate. So, there were two sets of negative control filter paper (DMEM only), two sets of Zika-inoculated filter paper untreated (positive control; T=0 min), two sets of Zika-inoculated filter treated with RGS for 45 minutes (test, T=45 min) and two sets of Zika-inoculated filter treated with RGS for 90 minutes (test, T=90 min).

Extraction of Zika Virus from Untreated (Positive Control) and RGS-Treated (Test) Filter Paper The untreated (T=0) and RGS-treated filter papers (T=45 and T=90 min) were separately extracted with PBS (1×). The filter papers before and after exposure were cut into small pieces and transferred into 50 ml sterile conical tubes for extraction. Extraction of the virus was performed according to standard established protocol (Butot et al, 2007). Briefly, 10 ml of sterile PBS was added into each 50 ml conical tubes containing the cut filter paper and vigorously vortexed. The tubes were incubated for 15 minutes at room temperature (RT) with intermittent vortexing, every 3 minutes. The tubes were then centrifuged at 5000 rpm for 5 min to pellet the filter paper debris, and the resulting supernatant filtered through 0.22-micron filter. The filtrates were stored at 4° C. for Zika virus activity analysis using 3-[4.5-dimethyl-2-thiaozolyl]-2-5-diphenyl-2H-tetrazolium bromide (MTT) cytotoxicity bioassay.

MTT Bio-Assay or (3-[4.5-Dimethyl-2-Thiaozolyl]-2-5-Diphenyl-2H-Tetrazolium Bromide Cytotoxicity Bio-Assay The MTT assay is a colorimetric assay for assessing cell metabolic activity. NAD(P)H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color.

Untreated and RGS-treated Zika virus filtrates were plated in 96-well tissue culture plate containing Vero cells at a seeding density of $6\times10^3$ cells per well, in final volume of 200 µl of DMEM. The cultures were incubated at 37° C. in humidified chamber with constant 5% $CO_2$, until the wells with T=0 filtrate showed 70% cells death (CPE). Then 20 µl of sterile MTT (5 mg/ml in PBS) solution was added to each well and the plates further incubated for 3 hours at 37° C. The spent DMEM medium was discarded by dumping it out and plates blotted dry. The resulting formazan crystals from attached Vero cells were then dissolved, by adding 100 µl of 1:2 mixture of dimethyl sulfoxide (DMSO) and ethanol. The absorption of the resulting formazan crystals solution was determined by reading its optical density (OD) at 490 nm, corrected to its 650 nm reading (Spectra Max 340 PC plate reader from Molecular Device Instruments). From the MIT solution absorption readings for negative Zika virus control (wells with no virus) and with Zika virus (filter paper filtrates) host cell growth was calculated for T=45 and T=90 minutes RGS treatments. The results are summarized below.

Results and Discussion

Results for Zika Virus Study

Figure 8:
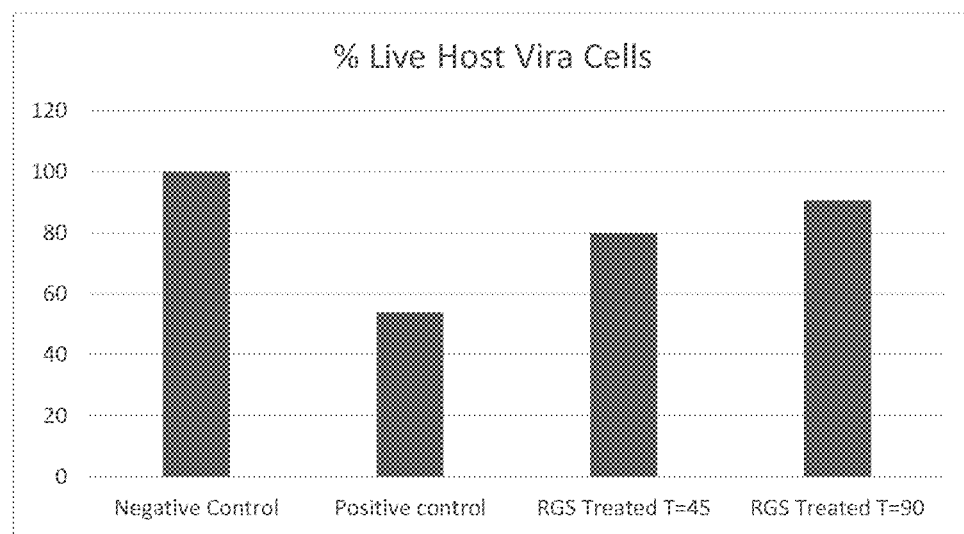
FIG. 8 is a graph of host cell count after exposing to filter paper extracts of negative control, positive control and RGS-treated Zika virus.

The cell viability of negative control wells (Vero cells with no virus) was compared with that of cells exposed to filter papers extracts of Zika virus from timepoints, T=0, 45 and 90 minutes. As observed, the untreated virus extract (T=0) caused approximately 50% cell death (toxicity), due to cytopathic effect (CPE) resulting from active virus infecting the Vero cells (Table 4). While virus extracts from RGS-treated Zika filter papers caused less Vero cells death because of deactivation of the Zika virus from RGS treatment. The host cell count corresponding to the negative control (no Zika), positive control (Zika not treated with RGS) and the two RGS-treated Zika are shown in FIG. 8 and Table 1. Compared to the positive control (Zika virus not treated with RGS), the 45 min and 90 min RGS-treatment deactivated Zika significantly (Table 4).

The percentage mortality of host cell is much less for T=90 treatment (9.45%) compared to T=45 treatment (20.14%) (Table 1). This means that more Zika is deactivated for 90 minutes treatment, compared to 45 minutes treatment, as expected. The normalization of the host cell mortality to the host cell mortality in negative control suggests 56.34% and 79.51% deactivation of Zika virus from 45 minutes and 90 minutes of RGS treatment, respectively (Table 1). As expected, the Vero cells exposed to the positive control Zika virus extract (T=0) showed maximum Vero cell death compared to filter paper extracts from the two RGS-treated Zika virus (T=45 and T=90).

TABLE 1

Host cell count from Zika-negative,
Zika-positive, and Zika-RGS treatments

| Treatment | % Live Host Cell | % Host cell Mortality | % RGS Deactivation of Zika virus (Normalized) |
|---|---|---|---|
| Negative Control | 100 | 0 | 0 |
| Positive control | 53.87 | 46.13* | 100** |
| RGS Treated T = 45 | 79.86 | 20.14* | 56.34** |
| RGS Treated T = 90 | 90.55 | 9.45* | 79.51** |

*normalized to negative control host cell count.
**normalized to positive host cell mortality.

Figure 9:
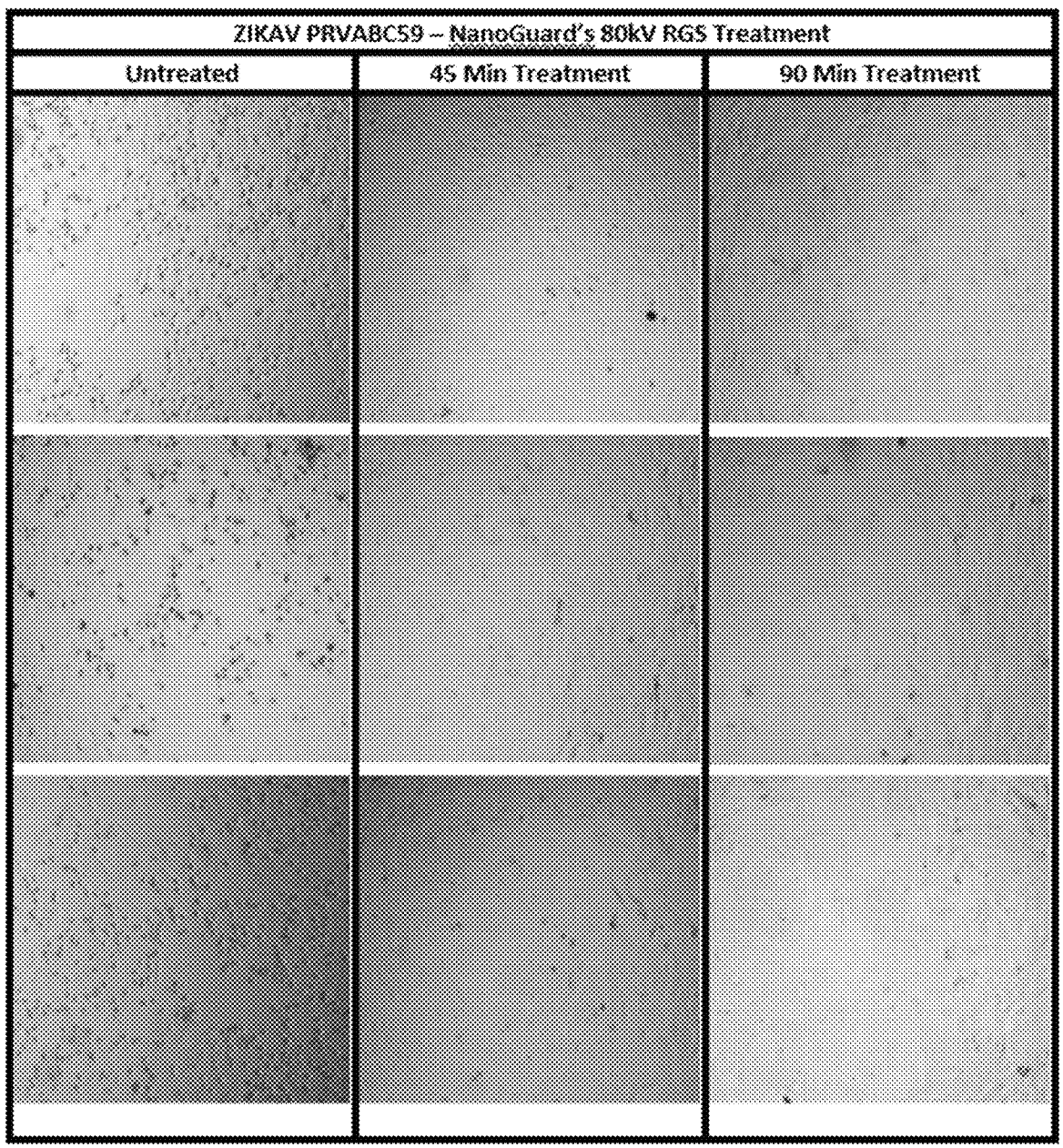
FIG. 9 is a set of microscopic photo images of three wells each of Vero cells exposed to filter paper extracts from untreated (positive control, T=0) and RGS-treated Zika virus. The dots on the photograph are Vero cells altered due to the cytopathic effect of the Zika virus.

FIG. 9 shows the microscopic photo images of wells of Vero cells (in triplicate) exposed to positive control (T=0) and RGS-treated Zika virus filter papers extracts. The cell death results shown in FIG. 8 matches with the microscopic images (FIG. 9).

Conclusion

The results from this study demonstrates that RGS treatment significantly deactivates Zika virus. A 90 minutes RGS treatment reduces Zika virus by approximately 80%. Thus, RGS treatment could effectively deactivate pathogenic viruses on surfaces, spaces, food, feed, medical equipment etc. RGS technology is an effective antiviral treatment against environmental, medical and food-borne viruses.

Example 3: *Salmonella enterica* (Newport) Bacteriophage Deactivation Using Reactive Gas (RGS): Use of SBA 1781 Bacteriophage Model to Determine the Effectiveness of RGS as an Antiviral Agent In this study, *Salmonella enterica* Bacteriophage (SBA 1781 phage virus) was used to evaluate the effectiveness of RGS in deactivating viruses.

Materials and Methods

Host Bacteria: *Salmonella enterica* (Newport strain, ATCC 6962), purchased from American Type Culture Collection (ATCC), Manassas, Va. Bacteriophage, SBA 1781: ATCC designation PTA-5282 was also purchased from ATCC.

Growing *Salmonella enterica* Culture (Host Bacteria)

The *Salmonella enterica* (ATCC 6962) is the natural bacterium host for bacteriophage, SBA 1781. The *Salmonella enterica* bacteria (in a vial) that was purchased from ATCC was reconstituted by adding 1 ml of fresh broth medium (1% Tryptone, 0.1% Yeast Extract, and 0.8% NaCl in distilled $H_2O$). The reconstituted bacteria culture (100 µl), was withdrawn from the vial and used to inoculate 10 ml of same broth medium in a culture glass tube with loose cap. The inoculated broth was grown overnight (18-20 hours) at 37° C. in a temperature-controlled incubator. The resulting *Salmonella enterica* overnight culture, was then used for propagation of bacteriophage, SBA 1781.

SBA 1781 Bacteriophage Propagation

The bacteriophage, SBA 1781 was propagated in its natural host cells, the *Salmonella enterica* culture, using the ATCC recommended procedure. Briefly, the host bacterial culture cells were grown overnight at 37° C., in broth as described above. Thereafter, 1.0 ml of bacterial culture cells suspension was added to the surface of agar plates and gently tilted to ensure the entire surface coverage with host bacterial cells. The excess liquid was then aspirated from the agar plates and the plates allowed to moist dry. Suspensions of various dilutions of *Salmonella* phage (SBA 1781) in broth were spotted on the surface of agar plates and incubated overnight at 37° C. The following day, the bacteriophage was harvested by adding 5 ml of fresh broth media per plate and incubated at 4° C. for 1 hour with periodic gentle shaking. The extract (suspension) from each plate was collected and transferred to a 50 ml sterile polypropylene tube, and another 5 ml fresh media added to each plate for a second extraction (20 minutes) at 4° C., with periodic gentle shaking. The two extracts from each plate were pooled in 50 ml conical tubes and the plates discarded. The pooled suspension was centrifuged at 5000×g for 15 min at 4° C., to pellet the cellular and agar debris. The supernatants were then collected and passed through 0.22 µM Millipore filter to remove host bacteria cells. The resulting filtrates containing the recovered bacteriophage were stored at 4° C. for future experimental use.

RGS Deactivation SBA 1781 Bacteriophage

For deactivating *Salmonella* bacteriophage with RGS, 1 ml of filtered phage supernatant was spotted on a circular Whatman filter paper (diameter 90 mm), purchased from General Electric Company (GE Healthcare Life Sciences, Pittsburgh, Pa.). The filter papers were then air dried and one set of filter paper assigned as positive control [not treated with RGS or untreated (T=0)] and was processed for phage extraction. The remaining filter papers were made into three sets and each set treated with RGS using RGS for 30, 60 and 90 minutes, respectively at 80 kV. After RGS treatment, each set of filter papers were sliced into small pieces separately and placed in sterile 50 ml tubes. The bacteriophage from the filter papers were extracted with 5 ml per tube of sterile PBS (1×). The viral activity in the recovered filter paper extracts was determined by high-throughput screening, using clear 96-well flat bottom plates (purchased from Midwest Scientific (MidSci), St. Louis, Mo.) seeded with an overnight bacterial culture of the host cells (*Salmonella enterica*). The fresh grown *Salmonella enterica* culture was diluted to a cell density of 1000 cells/ml suspension in nutrient broth; and plated into 96-well plate (170 µl/well). This was immediately followed by addition of 30 µl of various dilutions of bacteriophage extract (suspension) to a final volume of 200 µl per well. The inoculated 96-well plate was incubated at 37° C. for overnight culture growth (18-20 hours). The overnight culture optical density (OD) was then read at 660 nm using Spectra-Vmax PC340 plate reader (Molecular Devise). The absorbance reading obtained were used for computing bacterial growth, as a measure of growth reversal due to deactivation of SBA 1781 virus phage by RGS. The negative (media broth alone) and positive (bacterial culture alone) controls, were also run in the same plate; and in turn used for evaluating bacterial growth inhibition by bacteriophage. Both untreated (positive control) and RGS-treated phage were compared with negative control wells (wells without phage) and percentage growth of *Salmonella enterica* (viabilities) calculated for all treatment groups.

The effectiveness RGS in inactivating SBA 1781 was determined by comparing the bacterial (*Salmonella enterica*) growth difference (% viability) observed in extracts of RGS-treated and untreated (positive control) bacteriophage.

Results and Discussion

Figure 10:
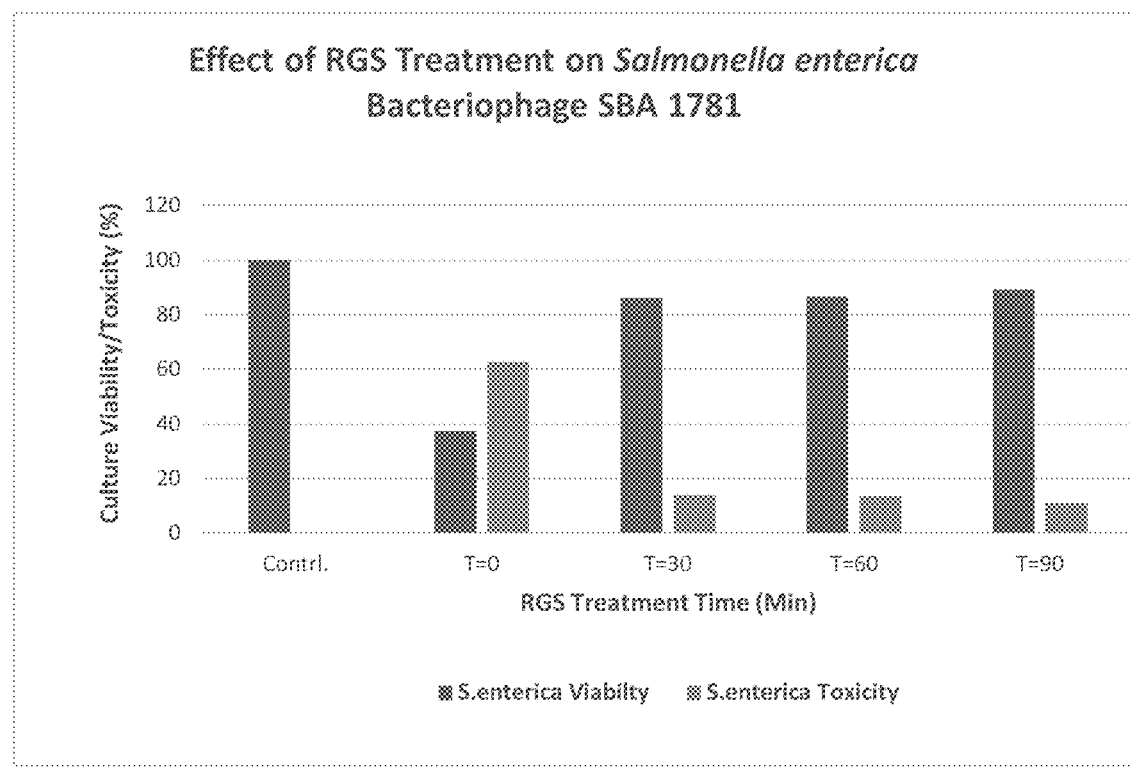
FIG. 10 is a graph showing deactivation of bacteriophage SBA 1781 using RGS.

RGS-treatment of *Salmonella enterica* bacteriophage (SBA 1781) significantly reduced its infectivity towards its target host cells (*Salmonella enterica*), thus allowing the host cells to grow (Table 2). The untreated SBA 1781 phage (positive control) was able to infect its bacterial host cells and cause lysis/death thus leading 63% mortality or alternatively 37% viability (survival rate) (Table 2 and FIG. 10). Exposure of phage to RGS for 30, 60 and 90 minutes drastically reversed the growth inhibition of host cells, as demonstrated by observed viabilities of 86%, 87% and 89%, respectively (Table 2). Exposure of phage to RGS for 30, 60 and 90 minutes drastically reversed the growth inhibition of host cells, as demonstrated by observed viabilities of 86%, 87% and 89%, respectively (Table 2).

TABLE 2

Determination of the RGS deactivation of bacteriophage using *Salmonella enterica* host cell viability

| | Absorbance Readings (OD at 660 nm) of *Salmonella enterica* Culture after 20 hours Growth | | | | |
|---|---|---|---|---|---|
| Replicate # | Media/Broth Negative Control | T= 0 min Positive Control | T = 30 min RGS Treated | T = 60 min RGS Treated | T = 90 min RGS Treated |
| Replicate 1 | 0.659 | 0.263 | 0.578 | 0.570 | 0.638 |
| Replicate 2 | 0.695 | 0.273 | 0.598 | 0.564 | 0.616 |
| Replicate 3 | 0.693 | 0.220 | 0.569 | 0.618 | 0.551 |
| Replicate 4 | 0.653 | — | 0.560 | 0.570 | 0.582 |
| Average OD 660 nm | 0.675 | 0.252 | 0.582 | 0.584 | 0.602 |
| % *S. enterica* Viability | 100 | 37 | 86 | 87 | 89 |
| % *S. enterica* Mortality | 0 | 63 | 14 | 13 | 11 |

TABLE 3

Host cell count from phage-negative, phage-positive, and the three phage-RGS treatments

| Treatment | % Live Host Cell | % Host cell Mortality | % RGS Deactivation of Zika virus (Normalized) |
|---|---|---|---|
| Negative Control | 100 | 0 | 0 |
| Positive control | 37 | 63* | 100** |
| RGS Treated T = 30 | 86 | 14* | 77.78** |
| RGS Treated T = 60 | 87 | 13* | 79.37** |
| RGS Treated T = 90 | 89 | 11* | 82.54** |

*normalized to negative control host cell count.

**normalized to positive host cell mortality.

The percentage mortality of host cell is much less for RGS-treated phage compared to positive control (Table 3). This means that more phage is deactivated by RGS treatment. The normalization of the host cell mortality to the host cell mortality in negative control suggests 77.78%, 79.37% and 82.54% deactivation of phage from 30 minutes, 60 minutes and 90 minutes of RGS treatment, respectively (Table 3). As expected, the host cells exposed to the positive control phage extract (T=0) showed maximum host cell death compared to filter paper extracts from the three RGS-treated bacteriophages (T=30, T=60 and T=90).

Conclusion

The preliminary results obtained from this study, clearly demonstrate the inhibitory effect of RGS on *Salmonella enterica* bacteriophage, SBA 1781 activity. The efficacy of RGS as an antiviral agent was evaluated by comparing the bacterial culture growth of bacteriophage in untreated control (positive control) and RGS-treated *Salmonella enterica* cultures. As demonstrated by the data, this technology is a tool for preventing the spreading of different groups of viruses.

Example 4: The Disinfection of MS2 Bacteriophage Virus Using RGS: Scaled-Up Pilot Generator System An RGS pilot generator was used to disinfect MS2 bacteriophage, a single stranded RNA virus spotted on and recovered from surfaces of 90 mm Whatman 5 filter papers. MS2 bacteriophage is an RNA virus that infects and lyses *Escherichia coli* (*E. coli*) and other bacterial members of Enterobacteriaceae. Since most human viral pathogens are RNA viruses, MS2 bacteriophage (non-human pathogen) was chosen as an optimal model for determining the effectiveness of RGS treatment on viral disinfection and inactivation.

The pilot system is an industrially hardened 8 kW generation system scaled from a 1 kW prototype technology system. The improved pilot system version has a significantly greater treatment chamber capacity with capabilities of generating greater amounts of reactive gas species (RGS) via dielectric barrier discharge (DBD) between ten 1.5-inch electrode gaps. For this study, the system was operated at 590 cubic feet per minute (cfm) and a voltage of 84 kV, which resulted in formation of 30±2 ppm of ozone as measured in the center of the container where samples were treated. Gas was passed through the plasma generator and then transported approximately 250 ft through a pneumatic conveying system and then through 4" PVC flexible tubing to a 20 ft standard shipping container that acted as the treatment chamber. The relative humidity (RH) and ambient temperature of air fed into the generation system were 50% and 70° F., respectively. The preliminary results and data obtained from this study show reduction of MS2 virus particles by 2-$\log_{10}$, indicating applicability of RGS as a tool for disinfecting viruses.

Materials

The host Bacteria: *Escherichia coli* (*E. coli*, strain K-12, ATCC 15597) was purchased from American Type Culture Collection (ATCC), Manassas, Va. The MS2 Phage: ATCC 15597-B1, was also purchased from ATCC. General laboratory consumables, reagents and supplies include: TSB medium broth, agar plates, top agar, pipettors, serological tubes and pipettes, SM phage buffer, syringes, 0.22 μM nylon syringe filters, black plastic SNAP PAK® containers, tweezers, hemostats, scissors, etc.

The medium includes: TSB Broth, bottom agar plates (100 mm plates) and top agar (3 ml/tube). The bottom agar includes: 1.5% agar in TSB broth (15 g per liter or 7.5 g per 500 ml). The top agar includes: 0.7% agar in TSB broth (7.5 g per liter or 3.75 g per 500 ml)

TABLE 4

SM Buffer

| Ingredients | 1 Liter | 500 ml |
| --- | --- | --- |
| NaCl | 5.8 g | 2.9 g |
| MgSO4 · 7H2O | 2.0 g | 1.0 g |
| 1M Tris HCl, pH 7.4 | 50 ml | 25 ml |
| 2% Gelatin (w/v) | 5 ml | 2.5 ml |

The SM buffer solution was sterilized with an autoclave cycle prior to use.

Methods

Growing Host Bacterial Culture for MS2 Propagation

The MS2 bacteriophage host bacterium used in this study was *Escherichia coli* (*E. coli*, strain K-12, ATCC 15597). The *E. coli* (ATCC 15597) in its original vial was purchased from ATCC and reconstituted by adding 1 ml of fresh broth medium (1% tryptone, 0.1% yeast extract, and 0.8% NaCl in de-ionized (DI) water). The reconstituted culture (100 µl), was withdrawn from the vial and used to inoculate 10 ml of the same broth medium in glass culture tubes which were grown in a thermal incubator overnight at 37° C. The resulting *E. coli* culture was then used for propagation of MS2 bacteriophage for treatment and subsequent titrated plaque assays for viruses recovered from untreated/treated samples.

MS2 Bacteriophage Propagation

The Bacteriophage, MS2 (ATCC 15597-B1) was propagated in its bacterial host cells, *E. coli* (strain K-12, ATCC 15597), according to ATCC procedure without using a soft/top-agar overlay. The host bacterial culture cells were grown overnight in broth at 37° C., as described above. Subsequently, 1.0 ml of host bacterial cells suspension was added to the surface of each agar plate and gently tilted to ensure the entire surface coverage with host bacterial cells. The excess liquid was then aspirated from the agar plate and plates were allowed to dry. Solutions of various dilutions of MS2 phage suspension in broth were spotted on the surface of agar plates and incubated overnight at 37° C.

After overnight growth, plates showing significant host bacterial lysis by MS2 phage were processed for phage virus extraction using bacteriophage stabilization buffer (SM). The SM stabilization buffer (5 ml) was added to each agar plate and stored at 4° C. for 3 hours with periodic gentle shaking. The SM buffer suspensions were collected and transferred into 50 ml polypropylene tubes. A second aliquot of fresh SM buffer (5 ml per plate) was added into each plate followed by further incubation at 4° C. for 15 minutes with periodic gentle shaking. The buffer was collected and pooled together with previously removed buffer in the 50 ml tubes before discarding the plates. The pooled SM buffer-MS2 phage suspension was centrifuged at 5000×g for 15 minutes at 4° C. to sediment the cellular debris and agar pieces prior to collection of particulate-free virus-laden supernatant. The resulting supernatants were passed through a 0.22 µM nylon syringe filter to remove host bacteria cells, and the filtrate containing the recovered MS2 phage was stored at 4° C. for experimental use.

Treatment of MS2 Virus with RGS and Extraction of Residue Virus

The MS2 Bacteriophage supernatant (1 ml) obtained from plates and containing propagated virus particles was spotted onto the surfaces of several sterile 90 mm Whatman 5 filter papers. The filter papers were then allowed to dry in a fume hood and placed into a clean container for storage at 4° C. until experimental treatment. Immediately prior to treatment, the virus-laden filter papers were removed from the refrigerator and transported in a cooler filled with ice packs to the treatment container. The filter papers were aseptically removed from their storage container and were clamped with binder clips which had been threaded with cotton twine and hung from magnetic hooks in various locations in the 8'×8'×20' (length×width×depth) steel container. The container had a double door. The right door was completely open and out of the way, and a ½-inch-thick plywood bulkhead panel attached to a 2×4 frame was inserted into the container replacing the open door. A nominal 4" hole was cut into the upper right-hand corner of the plywood panel and a 4" metal duct was inserted through the hole into the container, the duct terminating at the midpoint of the container where it was supported. The 10-foot-long ridged duct was connected to the 4" PVC flexible tubing. The left door was cracked open (1.5 inches) to give the gas an outlet to escape.

After each treatment of the filter paper samples, the plasma generator was turned off, but the blowers were left on for an additional 10 minutes to purge residual reactive gases from the container. The samples were then removed into individual sterile plastic containers and taken in a chilled cooler to the laboratory for extraction of residual virus using SM buffer. For extraction, RGS treated and untreated papers were aseptically sliced into 0.5 cm wide strips which were stacked and subsequently cut into 50 ml sterile tubes. SM buffer (5 mL) was added to each tube and extraction was performed over the course of 10 minutes. Just after the buffer was added and at each 2-minute interval during the 10 minutes, each sample was gently pulse-vortexed for 15 seconds. Thereafter, the tubes were centrifuged at 5000 rpm at 4° C. The supernatant containing residual virus was then filtered through 0.22 µM nylon syringe filters into 15 ml sterile tubes for determination of viral concentration using an MS2 plaque assay.

Plating and Titrations of MS2 Bacteriophage

The *E. coli* culture was started by inoculating 10 ml of TSB broth with 100 µl of *E. coli* suspension in the same medium as described above and grown overnight in a 37° C. incubator. The following day, the overnight culture was used to start another fresh *E. coli* culture. 1 ml of the overnight culture was added to 9 ml of fresh TSB medium (1:10 dilution of overnight culture) and grown for 3 hours in the same conditions. This fresh culture was then diluted 1:5 in TSB medium and used as the bacteria hosts in the MS2 plaque assay. Several dilutions of the untreated and treated filter papers extracts were made and the concentrations of recovered MS2 virus were determined by plaque assay using TSB top agar and bottom agar plates.

Briefly, 0.15 ml of the 3-hour bacterial culture was diluted 1:5 in TSB and was added to 3 ml of melted top/soft agar maintained at 42-45° C. by a water bath, followed by addition of 15 µl of diluted MS2 phage extract. The mixture was then vortexed gently, poured on bottom agar plates, and allowed to solidify. The plates were then incubated upside down, overnight in a 37° C. incubator. The following day, the formed plaques (clear areas) on the plates were counted and results tabulated as indicated below.

Results

Experiment 1: Inactivation of MS2 Bacteriophage Supernatant

Filter paper #13A was the untreated control sample (T=0) while filter paper #9 (placed in front of the gas entry point to the sample container) was treated with RGS for 1 hour at 84 kV at 590 cubic feet per minute (CFM).

TABLE 5

Experiment 1 Results: MS2 Plaque-Forming-Units per ml (PFUs/ml)

| Samples | Treatment | MS2 Dilution | MS2 Plaque Counts/Plate | MS2 Concentration (PFUs/ml) |
|---|---|---|---|---|
| MS2 Supernatant | Starting Material | $1 \times 10^8$ | 228 | 1.52E+12 |
| Sample #13A | T = 0 sample (Untreated Paper) | $1 \times 10^8$ | 90 | 6.00E+11 |
| Sample #9 | T = 1 hr. (Treated Paper) | $1 \times 10^6$ | 112 | 7.47E+9 |

The MS2 concentration per ml value in the fifth column of the above table is obtained by dividing the plaque count by 0.015 ml (the volume of MS2 extract which was added to the 15 ml vial containing 0.15 ml of 1:5 dilution of 3 hours E. coli, and 3 ml top agar) then accounting for the MS2 dilution factor.

Experiment 2: Inactivation of MS2 Bacteriophage Supernatant

Filter paper #9 was the untreated control sample (T=0). The filter paper #1 (placed in front of the gas entry point to the sample container) and filter paper #3 (placed in the back-left corner of sample container) were treated with RGS for 3 hours at 84 kv at 590 CFM.

TABLE 6

Experiment 2 Results: MS2 Plaque-Forming-Units per ml (PFUs/ml)

| Samples | Treatment | MS2 Dilution | MS2 Plaques Counts/Plate | MS2 Concentration (PFUs/ml) |
|---|---|---|---|---|
| MS2 Supernatant | Starting Material (Inoculum) | $1 \times 10^8$ | 35 | 2.33E+11 |
| Sample #9 | T = 0 (Untreated) | $1 \times 10^8$ | 4 | 2.67E+10 |
| Sample #1 | T = 3 hr. (Treated) | $1 \times 10^4$ | 38 | 2.53E+7 |
| Sample #3 | T = 3 hr. (Treated) | $1 \times 10^4$ | 96 | 6.40E+7 |

The MS2 concentration (PFUs/ml) value in the fifth column of the above table is obtained by dividing the plaque count by 0.015 ml (the volume of MS2 extract which was added to the 15 ml vial containing 0.15 ml of 1:5 dilution of 3 hrs. E. coli, and 3 ml top agar) then accounting for the MS2 dilution factor.

The tabulated data presented above are from two independent experiments performed on different dates. The results obtained from these two preliminary studies demonstrate that RGS treatment disinfects MS2 bacteriophage virus. As demonstrated by the results, exposure of MS2 phage to RGS reduced the virus load approximately 2-$\log_{10}$ for a 1-hour treatment and 3-$\log_{10}$ for a 3 hour treatment (Tables 5 and 6).

In Experiment 1, one untreated paper (sample 13A) was compared to one treated paper (sample 9) which was hung in the treatment container just in front of the gas inlet. Experiment 1 indicated a viable virus reduction of 98.8%, from $6.00 \times 10^{11}$ PFUs/mL to $7.47 \times 10^9$ PFUs/ml. In Experiment 2, one untreated paper (sample 9) was compared to two treated papers. The first treated paper (sample 1) was hung in the treatment container just in front of the gas inlet, while the second treated paper (sample 3) was hung in the back-left corner approximately 14 feet away from the gas inlet. The position of sample 3 carries significance because it likely saw significantly less turbulent air flow than sample 1 yet only had a slightly worse virus reduction percentage. Experiment 2 indicated viable virus reductions of 99.9% and 99.8%, from $2.67 \times 10^{10}$ PFUs/mL to $2.53 \times 10^7$ and $6.40 \times 10^7$ PFUs/mL for sample 1 and sample 3, respectively.

Figure 11:
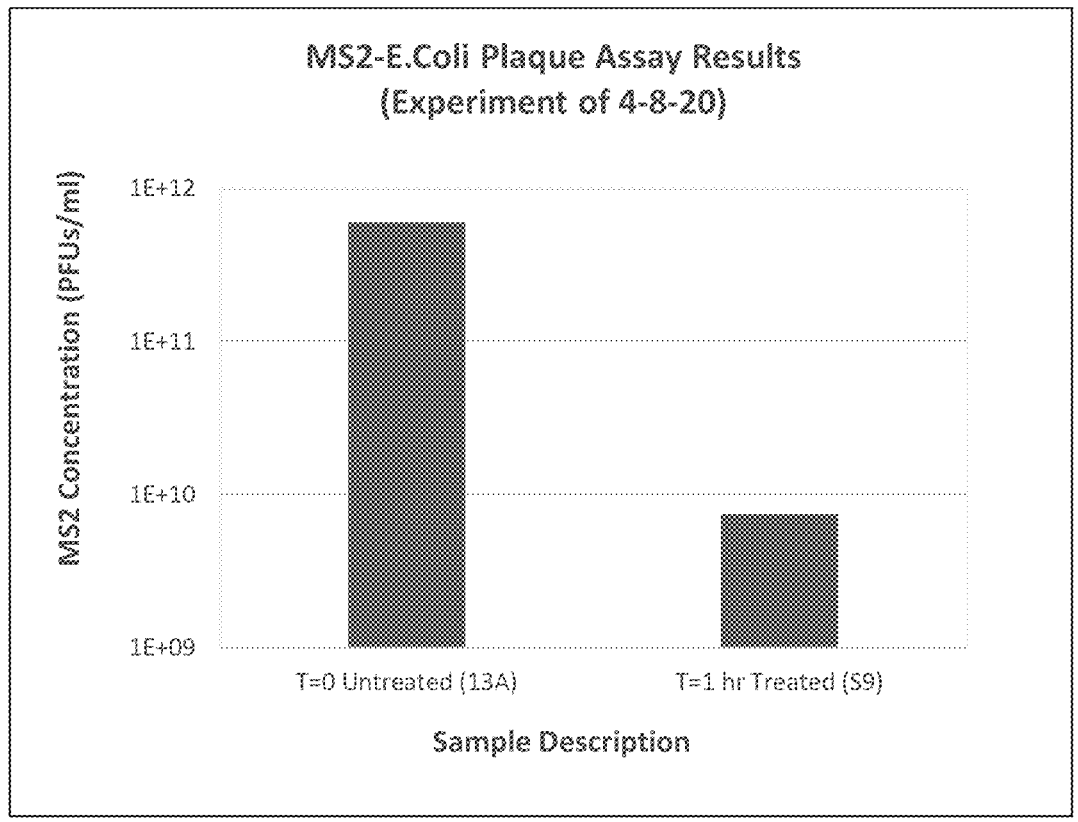
FIG. 11 is a graph showing deactivation of MS2 phage after 1 hour of exposure to RGS compared to untreated (T=0) MS2 phage.
Figure 12:
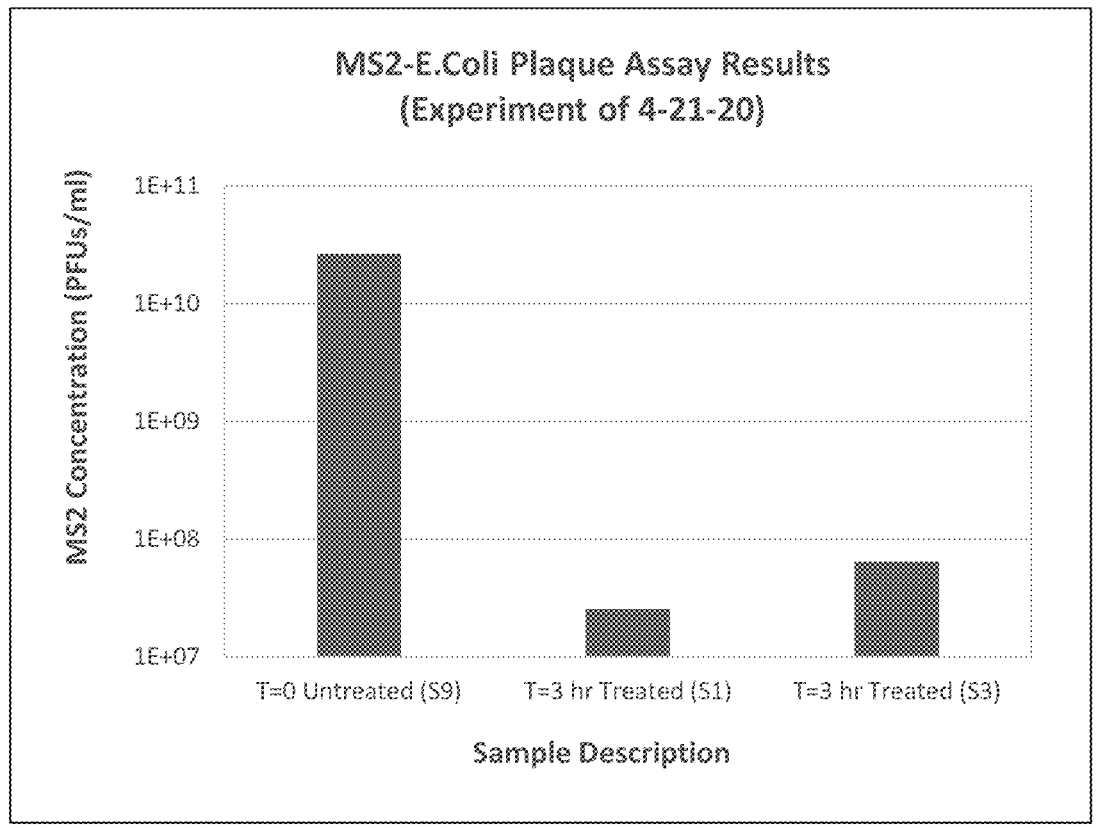
FIG. 12 is a graph showing deactivation of MS2 phage after 3 hours of exposure to RGS compared to untreated (T=0) MS2 phage.

Plating host E. coli cells with extracted MS2-bacteriophage viruses in this bacterial cell-based plaque assay provides a relatively easy method for quantifying virus recovery and reduction. Active MS2 phage infects its host cells and lyses (kills) them leading to formation of plaques, characterized by clear areas on the plates. Since each clear area (plaque) represents a single viral particle, plaque quantification allows for determination of virus titer in both control and experimental samples. As observed in the results shown in FIGS. 11 and 12, the extract of each T=0 untreated sample showed more plaques compared to the T=1-hour and T=3-hour treated samples. These results indicate exposing MS2 virus to RGS reduces their PFUs up to 3-$\log_{10}$ compared to the corresponding untreated sample extracts.

Conclusion

The results obtained from this study clearly demonstrate the reduction of MS2 bacteriophage viability by RGS treatment. Two independent experiments have indicated that RGS deactivates RNA viruses on surfaces at pilot-scale.

Example 5: The Effect of Reactive Gas Produced at 60 kV on Bacillus atrophaeus Spores at 60, 120 and 180 Minutes at Standard-Flow B. atrophaeus spores are considered one of the most difficult microorganisms to kill. The following experiment demonstrates the ability of reactive gas to kill any microorganisms, including viruses. Additional experiments show the killing of bacteria, which also shows the ability of reactive gas to kill viruses, since the composition of viruses and bacteria is similar.

Paper strips (Mesa Labs, Inc. Lakewood, Colo.) inoculated with B. atrophaeus spores were exposed to reactive gas (RGS) for 60, 120 and 180 minutes. The RGS was generated at 60 kV in a modified one-pass valve orientation. The amount of ozone produced is proportional to the total amount of RGS produced at a fixed voltage, and is easily quantified with available equipment, so ozone is used to track changes in the concentration of RGS.

After beginning plasma generation, RGS was accumulated until the amount of ozone was 350 ppm. At this point, the seal on the exhaust valve was opened slightly to allow a small volume of gas to escape and be replaced by ambient air, likely drawn through door seams in the plasma generator housing. This resulted in an increased flow rate of 25 to 28 cubic feet/minute (cfm) and a drop in ozone stabilizing at 250 ppm with only minor fluctuations. Samples were removed by closing the valves to the sample contactor while allowing RGS generation to continue circulating through the system. Ozone peaked near 350 ppm during brief sample removal (1 to 2 minute duration) but quickly stabilized to 250 ppm after resuming flow to the sample contactor.

Figure 13:
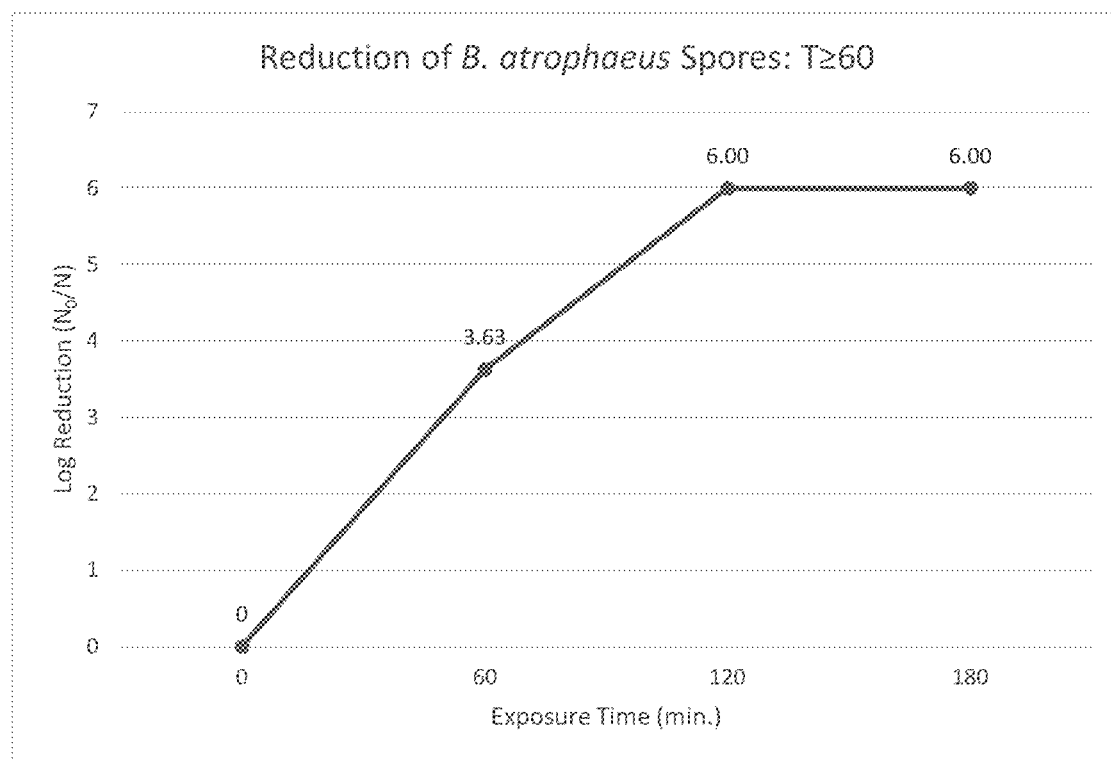
FIG. 13 is a graph showing the reduction of *B. atrophaeus* spores over exposure time.

Mesa Labs estimates that each strip contains $1.8 \times 10^6$ spores. Experimental controls processed by the procedure recommended by Mesa Labs measured an average of $1.0 \times 10^6$ spores/strip. At all timepoints, the measured final counts were 0 colony forming units (cfu) after the standard 48-hours. Plates were retained for observations. On the third day, samples which had been exposed to RGS for 60 minutes had a modest spore population. Samples exposed for a longer duration had no change. The final results are in FIG. 13 and Table 7 below.

TABLE 7

| Sample | Exposure Time (min.) | Log Reduction | Final Population |
|---|---|---|---|
| +CTRL | 7 | 0 | 0 | 1.22E+06 |
| +CTRL | 8 | 0 | 0 | 7.75E+05 |
| T = 60 | 1 | 60 | 3.63 | 2.35E+02 |
| T = 120 | 2 | 120 | 6.00 | 0 |
| T = 180 | 3 | 180 | 6.00 | 0 |
| T = 180 | 4 | 180 | 6.00 | 0 |
| T = 180 HF | 5 | 180 | 6.00 | 0 |
| T = 180 HF | 6 | 180 | 6.00 | 0 |

Figure 14:
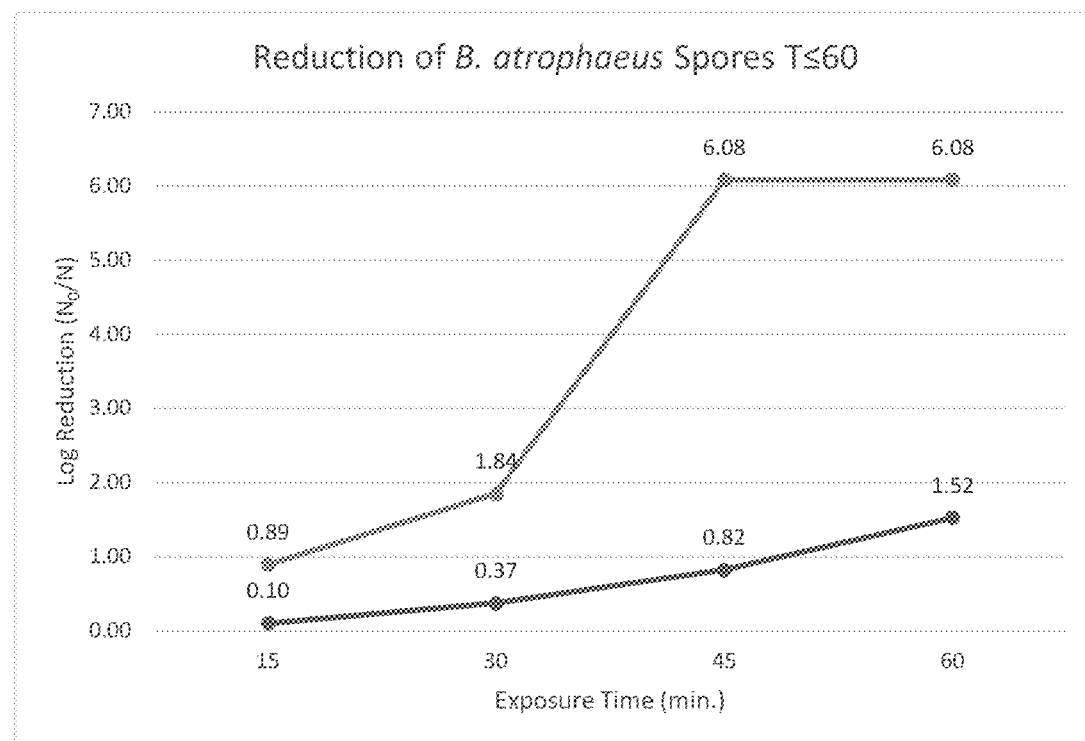
FIG. 14 is a graph showing the reduction of *B. atrophaeus* spores over exposure time for a high-flow system (orange) and a standard-flow system (blue).

Example 6: The Effect of Reactive Gas Produced at 60 kV on *Bacillus atrophaeus* Spores at 15, 30, 45 and 60 Minutes at Standard-Flow and High-Flow Paper strips (Mesa Labs, Inc. Lakewood, Colo.) inoculated with *B. atrophaeus* spores were exposed to reactive gas (RGS) for 15, 30, 45 and 60 minutes. The RGS were generated under the same conditions as Example 5. Two sets of paper strips received the same treatment conditions and time, but in different locations within the flow system. One set, "standard-flow," was suspended with binder clips looped on S-carabiners suspended from a wire rack placed in top (widest) portion of the sample contactor. A second set, "high-flow," was placed between the junctions of the sample contactor's effluent 90° steel elbow. The results are summarized in FIG. 14 and Table 8 below.

TABLE 8

| | Sample | Exposure Time (min.) | Log Reduction | Final Population |
|---|---|---|---|---|
| | | 9 | 0 | 0 | 1.20E+06 |
| Standard-Flow | 1 | 15 | 0.10 | 9.56E+05 |
| | 2 | 30 | 0.37 | 5.16E+05 |
| | 3 | 45 | 0.82 | 1.83E+05 |
| | 4 | 60 | 1.52 | 3.62E+04 |
| High-Flow | 5 | 15 | 0.89 | 1.56E+05 |
| | 6 | 30 | 1.84 | 1.72E+04 |
| | 7 | 45 | 6.08 | 0 |
| | 8 | 60 | 6.08 | 0 |

Data Compilation of Examples 5 and 6

Figure 15:
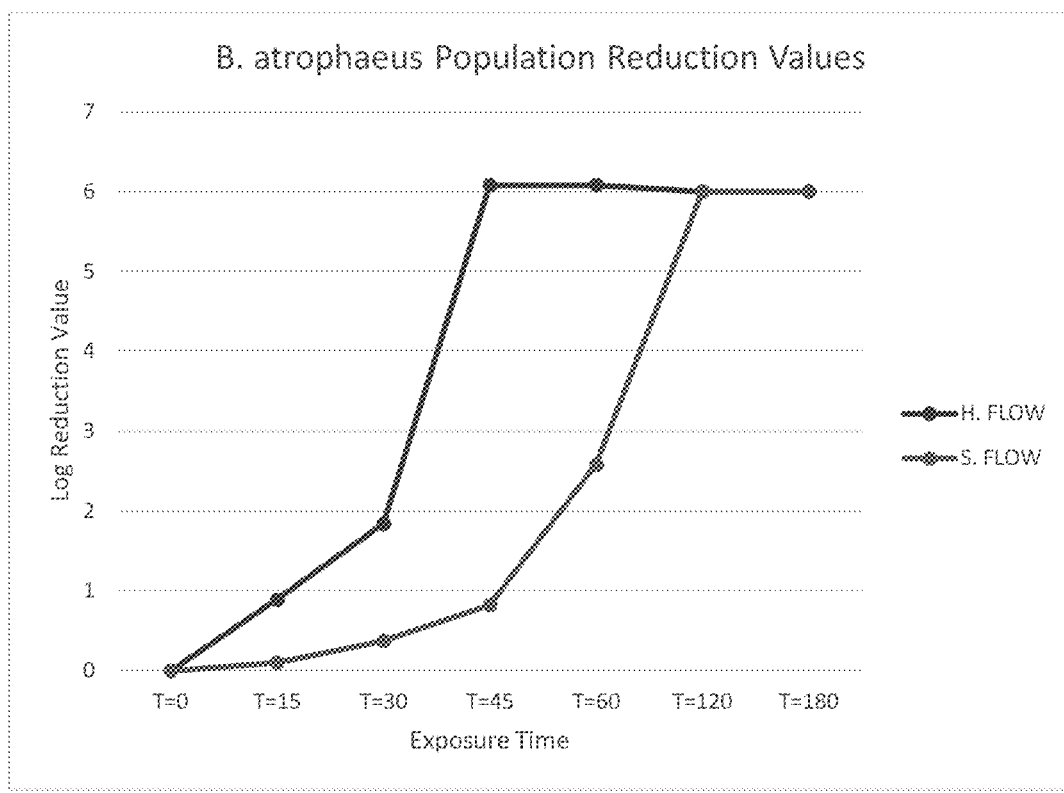
FIG. 15 is a graph showing the log reduction of spores over exposure time for a high-flow system (orange) and a standard-flow system (blue).
Figure 16:
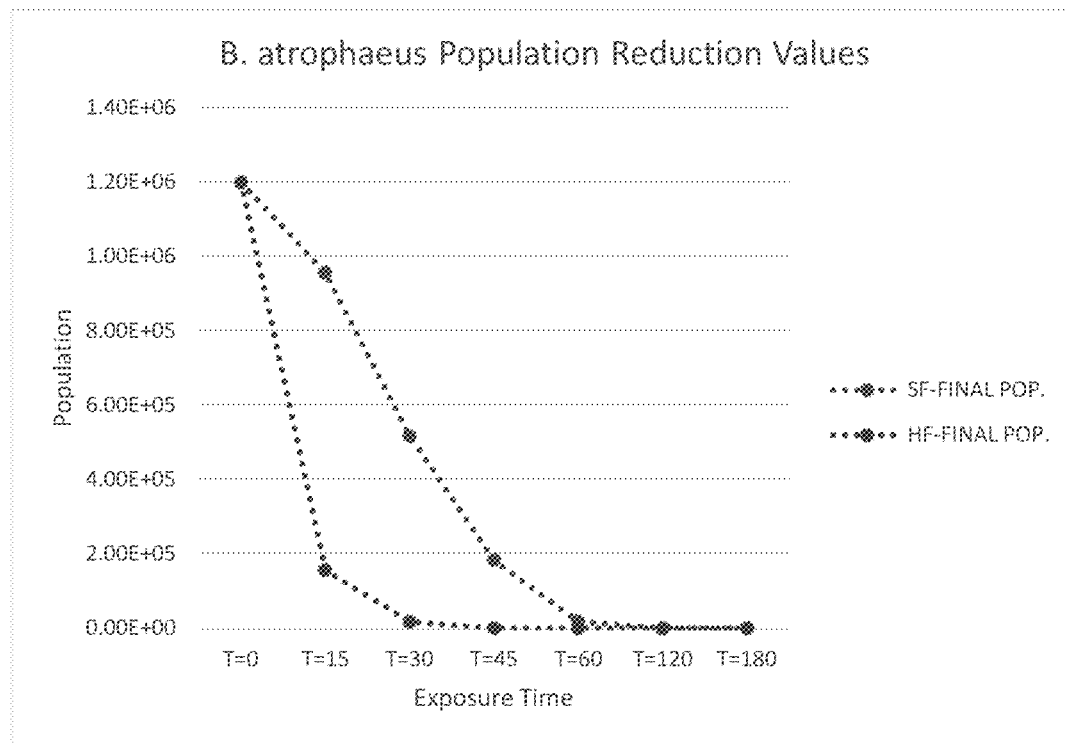
FIG. 16 is a graph showing the population of *B. atrophaeus* spores over exposure time for a high-flow system (orange) and a standard-flow system (blue).

Datapoints from the Examples 5 and 6, compiled in FIGS. 15 and 16, and Tables 9 and 10, show the reduction curve for all timepoints investigated in both high-flow and standard-flow conditions. Slight differences may be seen in datapoints between the individual and compiled summaries. Any overlapping timepoint replicates were averaged. The data set is displayed both as log-reduction and change in population, which are simply inverse functions representing the same trend.

Standard-flow conditions resulted in a gradual population reduction, reaching a reduction of roughly 2.5 logs in 60 minutes. Exposure at 120 and 180 minutes resulted in a complete reduction of the E+06 population. Under these experimental conditions, a 1 to 2 hours exposure was able to effectively eliminate a spore population level that would be comparable to commonly encountered contamination levels.

High-flow conditions resulted in a higher rate of reduction than standard-flow. The high-flow conditions were able to reduce the same population in roughly half the time. This is demonstrated when comparing the final population of high-flow at 30 minutes (N=1.72E+04) against the standard-flow at 60 minutes (N=1.82E+04). High-flow conditions eliminated the entire spore population after 45 minutes of exposure, whereas the standard-flow conditions did not reach total elimination until somewhere between 1 and 2 hours. By extrapolation, complete reduction by RGS exposure under standard-flow of an E+06 population would be expected to occur at about 90 minutes.

Standard-flow was calculated to be a velocity of 80.2 feet/minute, while high-flow was calculated to be a velocity of 2281 feet/minute. In both examples, the temperature was 25 to 40° C. with a dew point of 5.3 to 6.7° C., giving a relative humidity of 39.3 to 40.8. Please note: The "E+" is scientific E notation, where the expression "mE+n" indicates a value of $m \times 10^n$.

TABLE 9

| | S. FLOW (Log Reduction) | H. FLOW (Log Reduction) |
|---|---|---|
| T = 0 | 0 | 0 |
| T = 15 | 0.1 | 0.89 |
| T = 30 | 0.37 | 1.84 |
| T = 45 | 0.82 | 6.08 |
| T = 60 | 2.58 | 6.08 |
| T = 120 | 6 | 6 |
| T = 180 | 6 | 6 |

TABLE 10

| | SF-FINAL POP. | HF-FINAL POP. |
|---|---|---|
| T = 0 | 1.20E+06 | 1.20E+06 |
| T = 15 | 9.56E+05 | 1.56E+05 |
| T = 30 | 5.16E+05 | 1.72E+04 |
| T = 45 | 1.83E+05 | 0.00E+00 |
| T = 60 | 1.82E+04 | 0.00E+00 |
| T = 120 | 0.00E+00 | 0.00E+00 |
| T = 180 | 0.00E+00 | 0.00E+00 |

Figure 17:
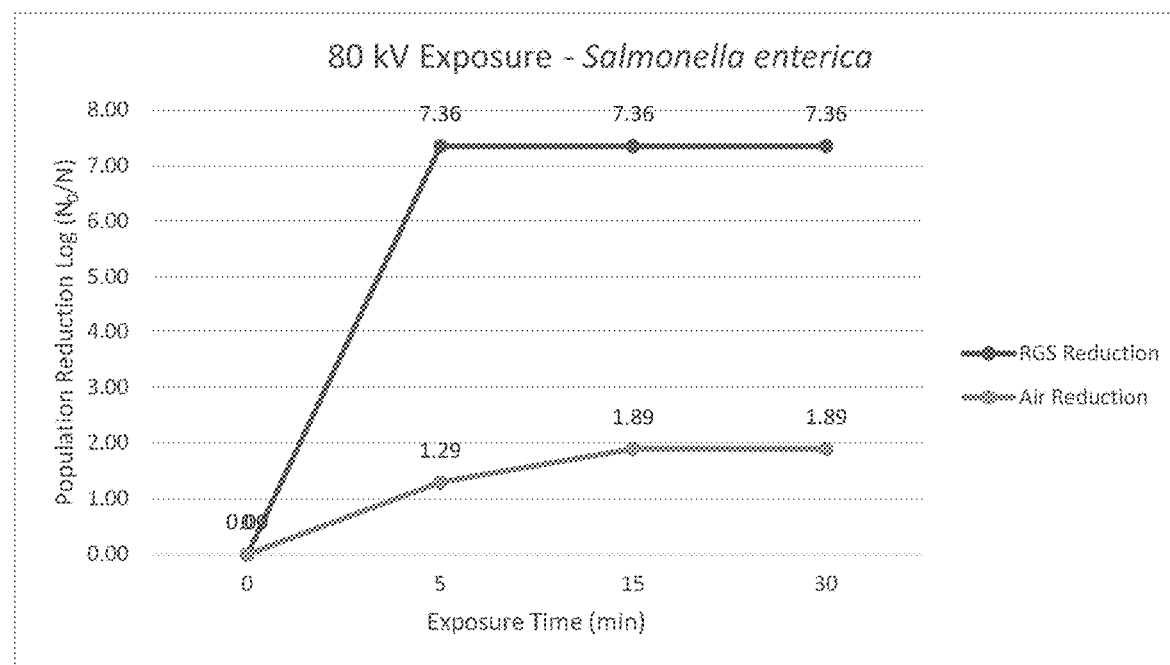
FIG. 17 is a graph showing reduction of *S. enterica* cells over exposure time for air reduction (orange) and reactive gas species reduction (blue).

Example 7: The Effect of Reactive Gas Produced at 80 kV on *Salmonella enterica* on Filter Paper Ten 10 mm Whatman filter papers were inoculated with 2.27E+6 *S. enterica* cells and exposed to reactive gas (RGS) over a 3-point time-course. Each sample included a batch of 10 filter papers treated simultaneously for 0, 5, 15 or 30 minutes with RGS generated at 80 kV. Three sets of filters were treated with only air for the respective time points for comparison. All control and experimental samples were inoculated immediately before placement into the treatment chamber, and placed immediately into extraction buffer after treatment. Reduction values for both RGS and air treatments expressed as the log of the change in population over time [$Log_{10}(No/N)$], are shown in FIG. 17 and Table 11 below.

TABLE 11

| Time | RGS Reduction | Air Reduction |
|---|---|---|
| 0 | 0.00 | 0 |
| 5 | 7.36 | 1.29 |
| 15 | 7.36 | 1.89 |
| 30 | 7.36 | 1.89 |

Figure 18:
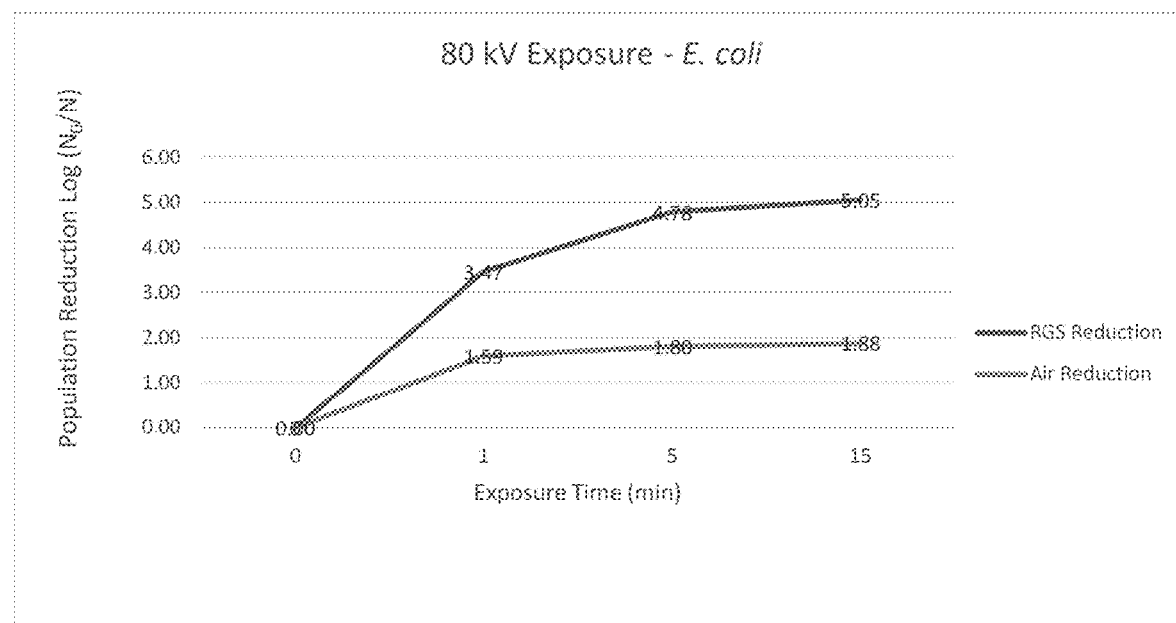
FIG. 18 is a graph showing reduction of *S. enterica* cells over exposure time for air reduction (orange) and reactive gas species reduction (blue).

Example 8: The Effect of Reactive Gas Produced at 80 kV on *Escherichia coli* on Filter Paper Example 8 was carried out under similar conditions as Example 7. Ten 10 mm Whatman filter papers were inoculated with 8.08E+6 *E. coli* cells and exposed to reactive gas species (RGS) over a 3-point time-course. Each sample included a batch of 10 filter papers treated simultaneously for 0, 1, 5 or 15 minutes with RGS generated at 80 kV. Three sets of filters were treated with only air for the respective time points for comparison. All control and experimental samples were inoculated immediately before placement into the treatment chamber, and placed immediately into extraction buffer after treatment. Reduction values for both RGS and air treatments expressed as the log of the change in population over time [$Log_{10}(No/N)$], are shown in FIG. 18 and Table 12 below.

TABLE 12

| Time | RGS Reduction | Air Reduction |
|---|---|---|
| 0 | 0.00 | 0 |
| 1 | 3.47 | 1.59 |
| 5 | 4.78 | 1.80 |
| 15 | 5.05 | 1.88 |

Example 9: The Effect of Reactive Gas Produced at 80 kV on *Escherichia coli* on Tryptone Soya Agar (TSA)

Figure 19:
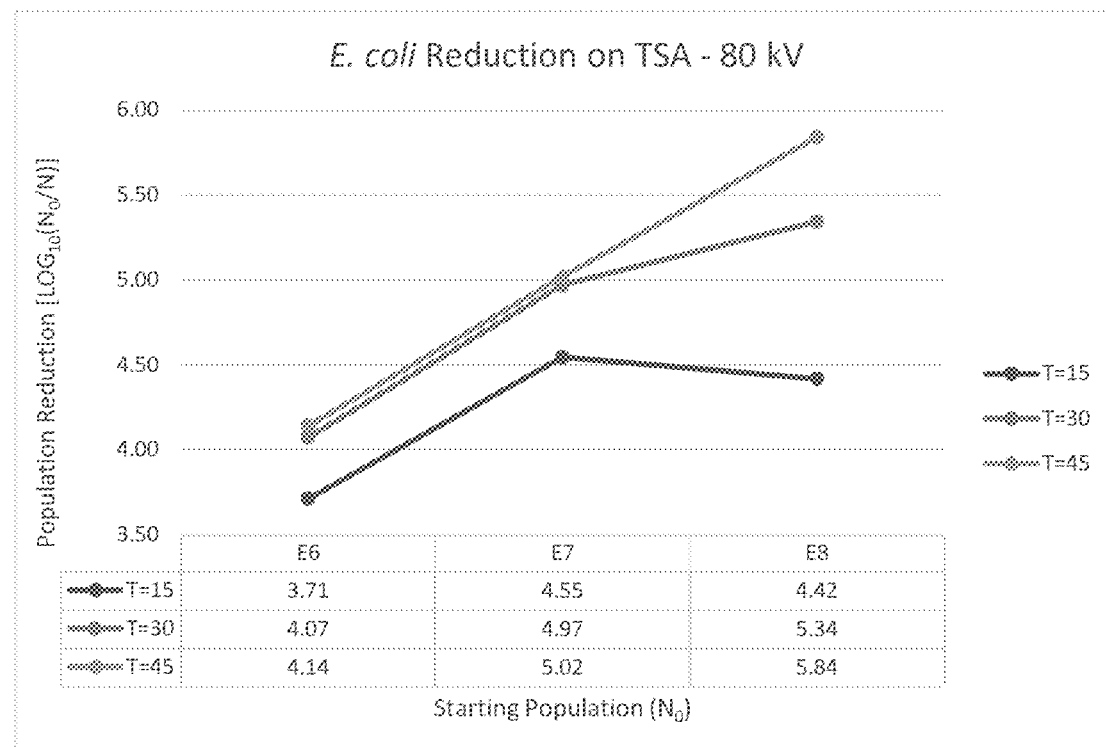
FIG. 19 is a graph showing the log reduction of *E. coli* populations for various initial populations.
Figure 20:
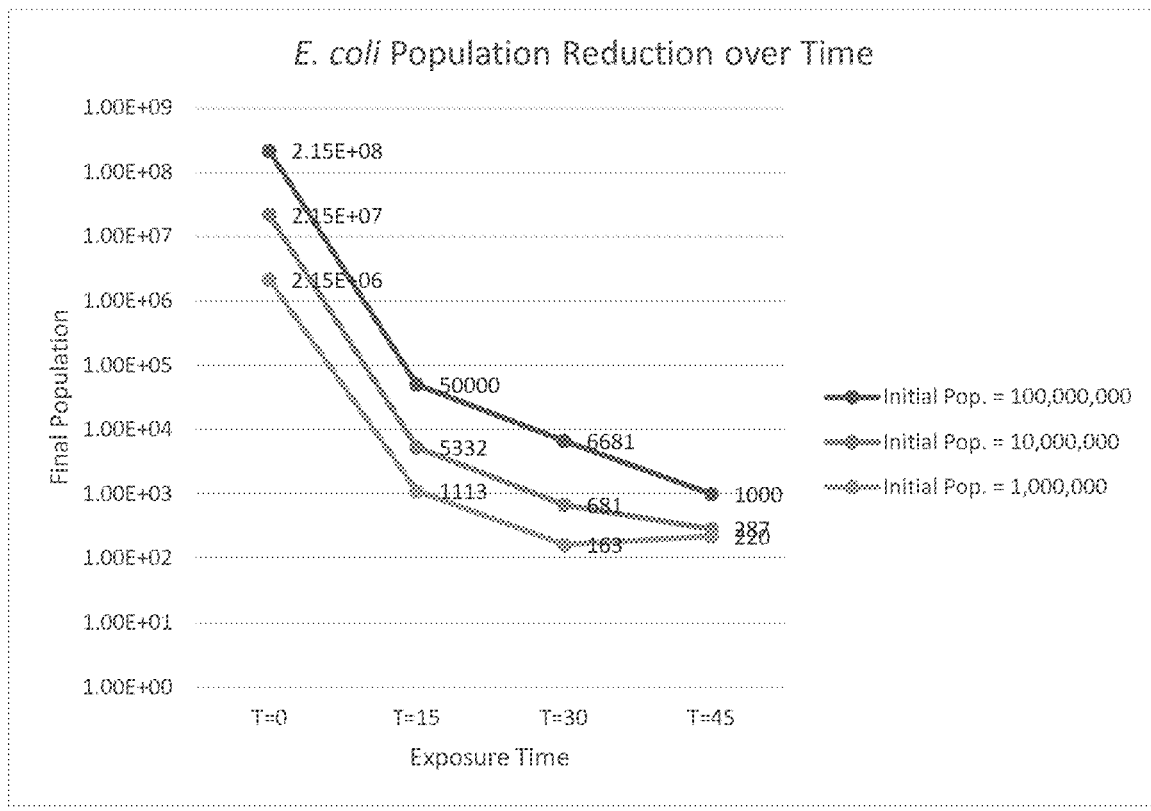
FIG. 20 is a graph showing the reduction of *E. coli* populations for various initial populations as a ratio of initial to final population.

An *E. coli* inoculum was prepared to an O.D. at 625 nm of 0.550. This density is estimated to be 1.8E+9 cells and experimentally confirmed to be 6.95E+9 cells. A series of 7, 1:10 serial dilutions were created from the inoculum resulting in a series of cell suspensions from E+9 cells down to E+2 cells. Three sets of initial population levels of E+8, E+7 and E+6 cells were inoculated onto TSA and treated for 15, 30 and 45 minutes with reactive gas (RGS). All control and experimental samples were inoculated immediately before placement into the treatment chamber, and placed immediately into extraction buffer after treatment. The results, reported in both log reductions and as a ratio of initial to final population, are shown in FIGS. 19 and 20. The detection limit of cells counts of E+2 or less prevented accurately distinguishing E+6 samples treated for 30 and 45 minutes, as well as E+7 samples treated for 30 and 45 minutes.

Example 10: The Effect of Reactive Gas Produced at 80 kV on *Escherichia coli* on Tryptone Soya Agar (TSA)

Figure 21:
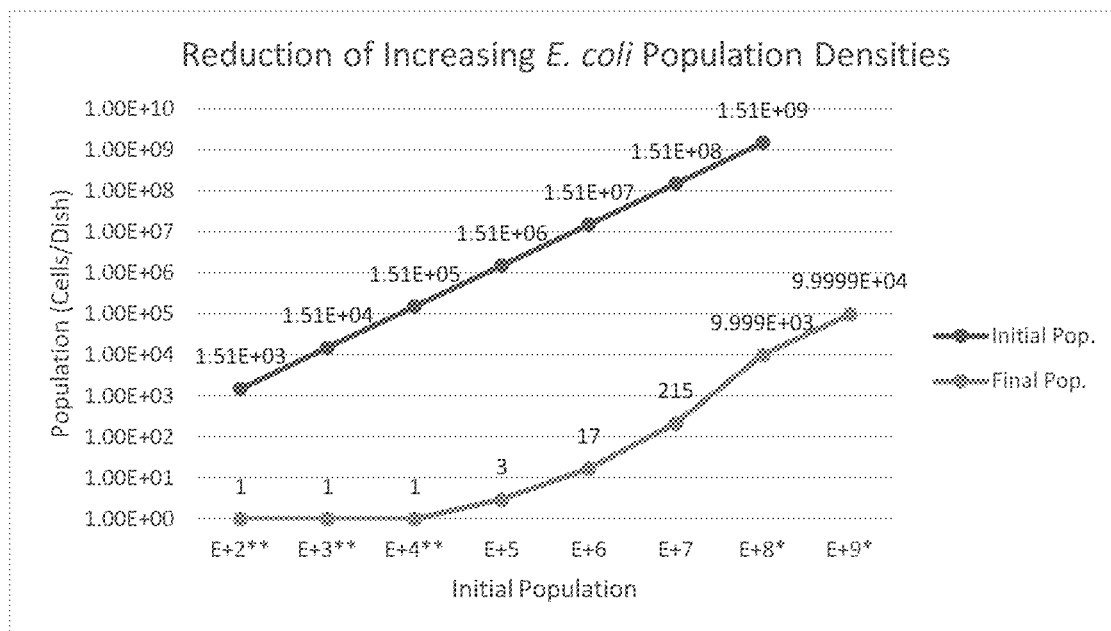
FIG. 21 is a graph showing the reduction of increasing *E. coli* population densities.
Figure 22:
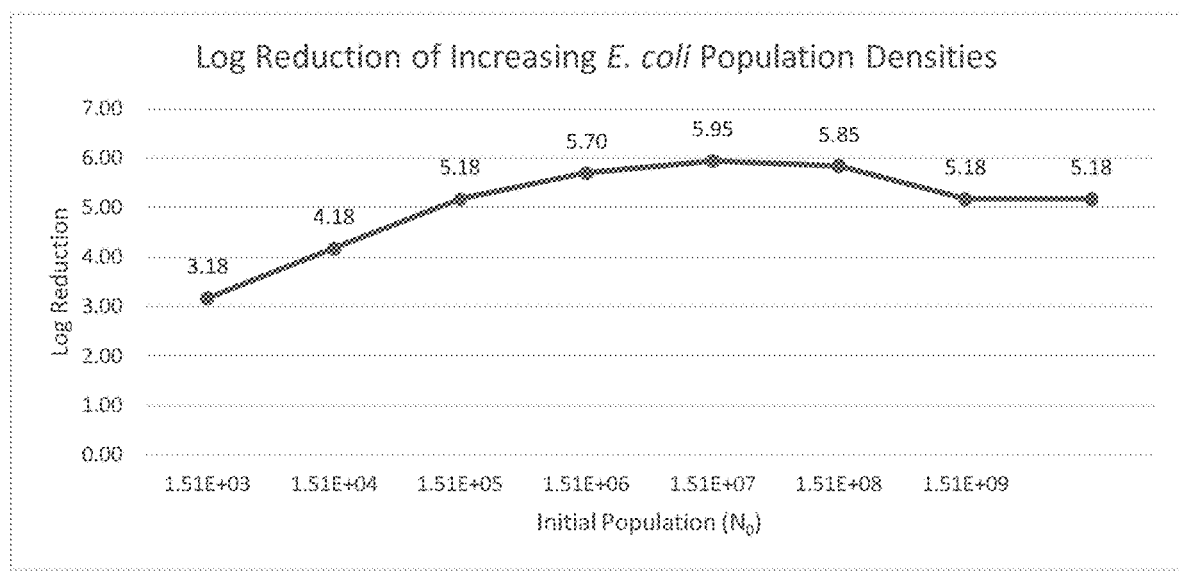
FIG. 22 is a graph showing the log reduction of increasing *E. coli* population densities.

*E. coli* cells cultured for 24 hours were concentrated to a starting density of 1.5E+10 and diluted in a series of 7, 1:10 dilutions. One set of 8 TSA plates was inoculated with 0.1 mL of each of the population dilutions resulting in a series of plates with cell populations beginning at 1.51E+9 through 1.51E+2 prior to a 25 minute reactive gas (RGS) exposure. A second set of plates was exposed to a 25 minute RGS exposure and inoculated with cells after the treatment in the same manner as the first series of plates. Reduction values of the pre-inoculated set indicate gross reduction due to all concomitant experimental factors. Reduction values of the post-inoculated plates indicate net reduction due to formation of peroxide radicals and acidification within the agar growth medium (note: most agar is 2.95% water). The results are displayed both as initial (No) versus final (N) population curves (FIG. 21) as well as by the magnitude of log reduction (FIG. 22). In FIG. 21, "*" indicates the cells are too numerous to count, and the number of cells is estimated by dilution scheme. In FIG. 21, "**" indicates that N=0, and a value of 1 used to obtain real number for log value.

Figure 23:
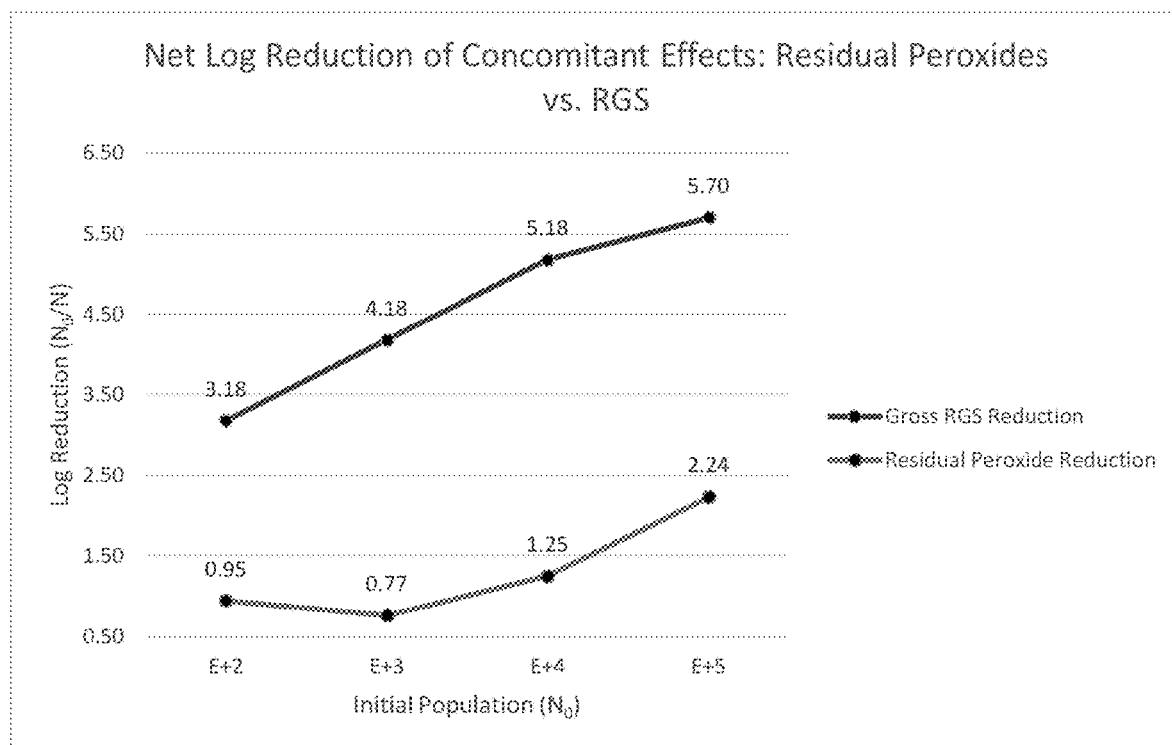
FIG. 23 is a graph showing the gross reactive gas species reduction and reduction by residual peroxide, for the four populations with peroxide effects within the countable range of experimental conditions.

FIG. 23 compares the gross reduction, and reduction by residual peroxide, for the four populations with peroxide effects within the countable range of experimental conditions. (Please note: The "E+" is scientific E notation, where the expression "mE+n" indicates a value of $m \times 10^n$.)

Example 11 (Prophetic)

It is desirable to verify that a surface that is contaminated with a virus has been disinfected by treatment with a reactive gas. In order to determine that the surface is disinfected, a first virus sample is taken from a surface prior to treatment with a reactive gas. This virus sample is stored in a cool, sterile container until it is ready to be tested. The surface is then contacted with a reactive gas. The reactive gas is produced by forming a high-voltage cold plasma (HVCP) from a working gas with a dielectric barrier discharge (DBD) system at a voltage of 20 kV to 150 kV and the reactive gas is transported at least 1 meter away from the HVCP. After the surface has been treated, a second virus sample is taken from the surface. A plaque assay test is performed on the first virus sample and the second virus sample. The number of plaques for each sample will be counted. The plaque forming units per volume (PFUs/mL) for each virus sample will be compared. By comparing the PFUs/mL of the treated and untreated paper, the $log_{10}$ reduction in virus is determined. If the virus concentration of the treated paper is $1.0 \times 10^7$ PFUs/mL and the virus concentration of the untreated paper is $1.0 \times 10^9$ PFUs/mL, then the treatment has achieved a 2-$log_{10}$ reduction. If the number of PFUs/mL in the second sample is too high, a second administration of reactive gas may be administered.

Alternatively, to determine if a reactive gas disinfects surfaces contaminated with virus, pieces of filter paper may be used to provide uniform virus samples. Two pieces of filter paper may be blotted with a solution containing a virus, preferably MS2 phage. One piece of the filter paper (RGS treated) may be placed in a chamber, which has surfaces to be treated. The surfaces in the chamber, including the filter paper, are contacted with a reactive gas. The reactive gas is produced by forming a high-voltage cold plasma (HVCP) from a working gas with a dielectric barrier discharge (DBD) system at a voltage of 20 kV to 150 kV and the reactive gas is transported at least 1 meter away from the HVCP. The other piece of filter paper (untreated) is stored in a cool, sterile container until it is ready to be tested. After the reactive gas treatment has been carried out, a plaque assay test is performed on the RGS treated and untreated filter papers.

REFERENCES

1. Puligundia Pradeep and Mok Chulkyoon, 2016. Non-thermal plasmas (NTPs) for inactivation of viruses in abiotic environment. Res. J. Biotech., 11(6): 91-96.
2. Wu Y., Liang Y., Wei K., Li W., Yao M., Zhang, J. and Grinshpun S. A., 2015. MS2 virus inactivation by atmospheric-pressure cold plasma using different gas carriers and power levels. Appl. Environ. Microbiol., 81: 996-1002.
3. Yasuda H., Miura T., Kurita H., Takashima K., and Mizuno A., 2010. Biological evaluation of DNA damage in bacteriophage inactivated by atmospheric pressure cold plasma. Plasma Process Polym., 7: 301-308.

4. Alshraiedeh N. H., Alkawareek M. Y., Gorman S. P., Graham W. G., and Gilmore B. F., 2013. Atmospheric pressure, nonthermal plasma inactivation of MS2 bacteriophage: effect of oxygen concentration on virucidal activity. J. Appl. Microbiol., 115: 1420-1426.
5. Bae S. C., Park S. Y., Choe W., and Ha S. D., 2015. Inactivation of murine norovirus-1 and hepatitis A virus on fresh meats by atmospheric pressure jets. Food Res. Int., 76: 342-347.
6. Cowling B J, et al., "Aerosol transmission is an important mode of influenza A virus spread." Nat Commun., 4, 1935 (2013).
7. Kuzmanovic, D. A., et al., "Bacteriophage MS2: Molecular Weight and Spatial Distribution of the Protein and RNA Components by Small-Angle Neutron Scattering and Virus Counting", Structure, Vol. 11, 1339-1348 (2003).
8. Wolf, C., et al., "Proxies to monitor the inactivation of viruses by ozone in surface water and wastewater effluent", Water Research, Volume 166 (2019).
9. Brie, A., et al., "Inactivation of murine norovirus and hepatitis A virus on fresh raspberries by gaseous ozone treatment", Food Microbiol., vol. 70, pg. 1-6 (2018).
10. Hudson J B, et al., "Development of a Practical Method for Using Ozone Gas as a Virus Decontaminating Agent" Ozone: Science & Engineering, 31, 216 (2009).
11. Ozone as a Disinfectant to Destroy Pathogens, like the Coronavirus (www.ozonesolutions.com/knowledge-center/use-ozone-as-a-disinfectant-to-destroy-pathogens-like-thecoronavirus.html) downloaded Mar. 13, 2020.
12. Ozone Effects on Pathogens (www.ozonesolutions.com/knowledge-center/ozone-effects-on-pathogens.html) downloaded Mar. 13, 2020.
13. Janis A. Muller, Mirja Harms, Axel Schubert, Benjamin Mayer, Stephanie Jansen, Jean-Philippe, Detlef Michael, Thomas Mertens, Olli Vapalahti, Jonas Schmidt-Chnasit and Jan. Munch (2017). Development of a high-throughput colorimetric Zika virus Infection Assay. Med. Microbiol Immunol 206: 175-185.
14. WHO. 2016. Zika virus Situation Report—5 Feb. 2016.
15. Rasmussen S A, Jamieson D J, Honein M A, Petersen L R (2016). Zika virus and Birth Defects-Reviewing the evidence for Causality. N. Engl J. Med 3741981-1987.
16. Muller J A, Harms M, Schubert A, Jansen S, Michael D, Mertens T, Schmidt-Chanasit J, Munch J, (2016). Inactivation and Environmental Stability of Zika virus. Emerg Infect Dis 22: 1685-1687.
17. Aubry M, Richard V, Green J, Broult J, Musso D (2016). Inactivation of Zika virus in Plasma with Amotosalen and Ultraviolet A Illumination. Transfusion 56: 33-40.
18. Butot S, Putallaz T, and Sanchez, G (2007). Procedure for Rapid Concentration and Detection of Entric Viruses from Berries and Vegetables. Appl Environ Microbiol 73 (1): 186-192.
19. Joelle Woolston, Adam R. Parks, Tamar Abuladze, Bradley Anderson, Manrong Li, Chandi Carte, Leigh Farris Hanna, Serena Heyse, Duane Charbonneau and Alexander Sulakvelidze, 2013. Bacteriophage lytic for *Salmonella* Rapidly Reduce *Salmonella* Contamination on glass and Stainless-steel Surfaces. Landes Bioscience; Bacteriophage 3: 3, e25697-1.
20. Gwyneth V. Carey-Smith, Craig Billington, Angela J. Cornelis, J. Andrew Hudson and Jack A. Heinemann, 2006. Isolation and Characterization of Bacteriophage Infecting *Salmonella* spp. FEMS Microbiol Lett 258: 182-186.
21. Nitzan Soffer, Tamar Abuladze, Joelle Woolston, Manrong Li, Leigh Farris Hanna, Serena Heyse, Duane Charbonneau and Alexander Sulakvelidze, 2016. Bacteriophage Safety Reduce Salmonell Contamination in Pet Food and Raw Pet Food Ingredients. Taylor& Francis Group, Bacteriophage 6: 3, e1220347.
22. Hakdong Shin, Ju-Hoon Lee, Hyeryen Kim, Younho Choi, Sunggi Heu and Sangryeol Ryu, 2012. Receptor Diversity and Host Interaction of Bacteriophage Infecting *Salmonella enterica* Serovar *Typhimurium*. Plos One, 7:8, e43392.
23. Ian Cock and Kalt F. R., 2010. A modified MS2 bacteriophage plaque reduction assay for rapid screening of antiviral plant extracts. Pharmacognosy Res. 2(4) 221-228.
24. "Influenza Type A Viruses". Centers for Disease Control and Prevention. https://www.cdc.gov/flu/avianflu/influenza-a-virus-subtypes.htm. Last reviewed Apr. 19, 2017, visited on Mar. 12, 2020.
25. EPA, "Guidance to Registrants: Process For Making Claims Against Emerging Viral Pathogens Not on EPA-Registered Disinfectant Labels", published on Aug. 19, 2016.

What is claimed is:

1. A method of disinfecting a surface suspected of contamination with a virus, comprising:
producing a reactive gas by forming a high-voltage cold plasma (HVCP) from a working gas with a dielectric baffler discharge (DBD) system;
transporting the reactive gas at least 1 meter away from the HVCP; followed by
contacting the surface with the reactive gas to disinfect the surface,
wherein a host infected with the virus had contacted the surface,
the reactive gas comprises (a) optionally ozone, and (b) at least one reactive or excited species other than ozone, and
effectiveness of the reactive gas at disinfecting is greater than that of the ozone content alone.

2. The method of claim 1, wherein the surface is an interior surface of a made-made structure.

3. The method of claim 1, wherein the host is a human or an animal.

4. The method of claim 1, wherein the host is a plant.

5. The method of claim 2, wherein the man-made structure comprises a room or a passage.

6. The method of claim 2, wherein the man-made structure comprises a vehicle.

7. The method of claim 1, wherein the contacting is carried out in a room having a volume of at least 8 cubic meters.

8. The method of claim 5, wherein the room is in a hospital.

9. The method of claim 1, wherein the surface is the surface of a medical device.

10. The method of claim 1, wherein the contacting is for 1 second to 24 hours.

11. The method of claim 1, wherein the virus is an RNA virus.

12. The method of claim 1, wherein the virus is selected from the group consisting of: rotavirus, rhinovirus, porcine reproductive and respiratory syndrome virus (PRRSV), African swine fever virus (ASF), hantavirus, norovirus, measles virus, ebola virus, influenza virus, avian virus, Zika virus, coronavirus, Middle East respiratory syndrome (ITERS) coronavirus, severe acute respiratory syndrome (SARS)

coronavirus, severe acute respiratory syndrome coronavirus 2 (SARS-CoV-2), papillomavirus, canine parvovirus, herpes simplex virus, chicken pox virus, cytomegalovirus, Epstein-Barr virus, smallpox virus, monkey pox virus and poliovirus.

13. The method of claim 12, wherein the virus is severe acute respiratory syndrome coronavirus 2 (SARS-CoV-2).

14. A method of disinfecting a surface contaminated with a virus, comprising:
  producing a reactive gas by forming a high-voltage cold plasma (HVCP) from a working gas with a DBD system;
  transporting the reactive gas at least 1 meter away from the HVCP;
  followed by contacting the surface with the reactive gas to disinfect the surface,
  wherein a host infected with the virus had contacted the surface,
  the reactive gas comprises (a) optionally ozone, and (b) at least one reactive or excited species other than ozone, and
  effectiveness of the reactive gas at disinfecting is greater than that of the ozone content alone.

15. The method of claim 14, wherein the virus is selected from the group consisting of: rotovirus, rhinovirus, porcine reproductive and respiratory syndrome virus (PRRSV), African swine fever virus (ASF), hantavirus, norovirus, measles virus, ebola virus, influenza virus, avian virus, Zika virus, coronavirus, Middle East respiratory syndrome (MERS) coronavirus, severe acute respiratory syndrome (SARS) coronavirus, severe acute respiratory syndrome coronavirus 2 (SARS-CoV-2), papillomavirus, canine parvovirus, herpes simplex virus, chicken pox virus, cytomegalovirus, Epstein-Barr virus, smallpox virus, monkey pox virus and poliovirus.

16. The method of claim 14, wherein the virus is severe acute respiratory syndrome coronavirus 2 (SARS-CoV-2).

17. The method of claim 1, wherein the contacting the surface is sufficient to produce at least a 2-$\log_{10}$ reduction by MS2 phage assay test.

18. A method of disinfecting a surface contaminated with a virus, comprising:
  (I) producing a reactive gas by forming a high-voltage cold plasma (HVCP) from a working gas with a DBD system;
  (II) transporting the reactive gas at least 1 meter away from the HVCP;
  (III) followed by contacting the surface with the reactive gas to disinfect the surface,
  (IV) obtaining a virus sample from the surface after the contacting, and
  (V) determining an amount of remaining virus after exposure to the reactive gas,
  wherein, if the surface is not disinfected by the contacting, repeating (I), (II) and (III) until the surface is disinfected,
  the reactive gas comprises (a) optionally ozone, and (b) at least one reactive or excited species other than ozone, and
  effectiveness of the reactive gas at disinfesting is Greater than that of the ozone content alone.

19. The method of claim 18, wherein the determining uses MS2 phage plaque assay test.

20. The method of claim 1, wherein the working gas is MA65.

* * * * *

UNITED STATES PATENT AND TRADEMARK OFFICE
CERTIFICATE OF CORRECTION

PATENT NO. : 11,896,731 B2
APPLICATION NO. : 17/017517
DATED : February 13, 2024
INVENTOR(S) : Mark A. Hochwalt It is certified that error appears in the above-identified patent and that said Letters Patent is hereby corrected as shown below:

In the Claims

Column 32, Line 29, please delete "baffler" and insert --barrier--

Column 32, Line 42, please delete "made-made" and insert --man-made--

Column 32, Line 66, please delete "(ITERS)" and insert --(MERS)--

Column 34, Line 27, please delete "Greater" and insert --greater--

Signed and Sealed this
Twenty-sixth Day of March, 2024

Katherine Kelly Vidal
*Director of the United States Patent and Trademark Office*